US006825930B2

(12) United States Patent
Cronin et al.

(10) Patent No.: US 6,825,930 B2
(45) Date of Patent: Nov. 30, 2004

(54) MULTISPECTRAL IMAGING SYSTEM

(75) Inventors: Paul J. Cronin, Charlestown, MA (US); Daniel Orband, Lynn, MA (US); Stephen D. Fantone, Lynnfield, MA (US); Peter J. Miller, Newburyport, MA (US)

(73) Assignee: Cambridge Research and Instrumentation, Inc., Woburn, MA (US)

( * ) Notice: Subject to any disclaimer, the term of this patent is extended or adjusted under 35 U.S.C. 154(b) by 87 days.

(21) Appl. No.: 10/163,233

(22) Filed: Jun. 4, 2002

(65) Prior Publication Data

US 2003/0223248 A1 Dec. 4, 2003

(51) Int. Cl.[7] .............................. F21V 9/00; G01J 3/10
(52) U.S. Cl. ...................... 356/328; 250/205; 362/231
(58) Field of Search ................................ 356/326, 328; 250/205; 362/231

(56) References Cited

U.S. PATENT DOCUMENTS

| 4,519,707 | A | | 5/1985 | Kuffer ........................ 356/326 |
|---|---|---|---|---|
| 4,669,878 | A | | 6/1987 | Meier ......................... 356/319 |
| 5,029,245 | A | * | 7/1991 | Keranen et al. ............. 356/328 |
| 5,066,124 | A | | 11/1991 | Wulf .......................... 356/312 |
| 5,257,086 | A | | 10/1993 | Fateley et al. .............. 356/328 |
| 5,970,424 | A | | 10/1999 | Kaffka et al. ................ 702/30 |
| 6,075,595 | A | * | 6/2000 | Malinen ...................... 356/328 |
| 6,118,562 | A | | 9/2000 | Lee et al. .................... 359/124 |
| 6,160,618 | A | | 12/2000 | Garner ........................ 356/318 |
| 6,192,062 | B1 | | 2/2001 | Sanchez-Rubio et al. ..... 372/92 |
| 2001/0052978 | A1 | | 12/2001 | Lewis et al. ................. 356/326 |

FOREIGN PATENT DOCUMENTS

| EP | 0 709 941 A1 | 5/1996 | ............. H01S/3/25 |
|---|---|---|---|
| WO | WO 00/25086 | 5/2000 | ............. G01B/9/02 |
| WO | WO 01/11343 | 2/2001 | |

OTHER PUBLICATIONS

Keranen et al., "Thirty–two Channel LED Array Spectrometer Module with Compact Optomechanical Construction," Technical Research Centre of Finland, Electronics Laboratory, Finland, SPIE vol. 1533 Optomechanics and Dimensional Stability (1991), pp. 122–128.

Stallard et al., "Construction of Filter Vectors for the Information–Efficient Spectral Imaging Sensor," Sandia National Laboratories, Albuquerque, NM, SPIE vol. 3438, pp. 172–182.

* cited by examiner

Primary Examiner—F. L. Evans
(74) Attorney, Agent, or Firm—Fish & Richardson P.C.

(57) ABSTRACT

The invention features a multi-spectral microscopy system for illuminating a sample with light of a selectable spectral content and generating an image of the sample in response to the illumination. The multi-spectral microscopy system includes a multispectral illuminator that provides output radiation having the selectable spectral content. A preferred set of optical arrangements for the multispectral illuminator generates the output radiation so that the spectral content of the output radiation is substantially uniform across its transverse profile. Furthermore, the multispectral illuminator can include monitoring optics and a corresponding detector array that independently monitors the output in each spectral band of the radiation produced by the multispectral illuminator. The monitoring provides calibration, feedback, and/or source aging information to insure robust and reliable performance for the multispectral illuminator. The multispectral microscopy system also includes a microscope which illuminates the sample with light derived from the output of the multispectral illuminator, and beam modification optics, which modify the output from the lamp prior to the microscope to increase the light efficiency of the microscope and fully exploit field of view and resolution of the microscope.

95 Claims, 11 Drawing Sheets

MULTISPECTRAL IMAGING SYSTEM

BACKGROUND

Applications in medicine, science, and engineering commonly use microscopy to determine information about a given sample. Such applications likewise exploit spectroscopic information when analyzing a sample. In particular, the optical response of a sample often depends on the spectral content of light illuminating the sample, and that spectral dependence provides additional information about the sample or components therein. Not surprisingly, it is often desirable to obtain both spatial and spectral information about a sample to more accurately identify or characterize different regions or components of the sample. For example, one may want to spatially resolve the optical response of a sample (e.g., the optical transmission) as a function of illumination light at a particular wavelength or superposition of wavelengths. Furthermore, the image of a sample at a particular wavelength or superposition of wavelengths may be useful in distinguishing and spatially isolating one component of the sample from other components of the sample.

In such applications, however, it is important that light intensity variations in the detected image can be properly associated with the sample. Accordingly, variations in the relative spectral content of the illumination light across its spatial profile should be minimized or carefully calibrated. Furthermore, any spectroscopic imaging system should provide robust and reliable performance, and efficiently exploit the available illumination light.

SUMMARY

The invention features a multi-spectral microscopy system for illuminating a sample with light of a selectable spectral content and generating an image of the sample in response to the illumination. The selection of the spectral content of the illumination and the image detection can be performed through an electronic control system. The multispectral microscopy system includes a multispectral illuminator that provides output radiation having the selectable spectral content. A preferred set of optical arrangements for the multispectral illuminator generates the output radiation so that the spectral content of the output radiation is substantially uniform across its transverse profile. In particular, the absolute intensity of the output radiation may vary across its transverse profile, but the relative spectral content of the radiation is substantially uniform across the transverse profile. Furthermore, the multispectral illuminator can include monitoring optics and a corresponding detector array that independently monitors the output in each spectral band of the radiation produced by the multispectral illuminator. The monitoring provides calibration, feedback, and/or source aging information to insure robust and reliable performance for the multispectral illuminator. The multi-spectral microscopy system also includes a microscope which illuminates the sample with light derived from the output of the multispectral illuminator, and beam modification optics, which modify the output from the lamp prior to the microscope to increase the light efficiency of the microscope and fully exploit field of view and resolution of the microscope. In preferred embodiments, the beam modifications optics provide independent and selectable control over the spot size and divergence cone of the illumination pattern on the sample.

We will now summarize different aspects, features, and advantages of the invention.

In general, in one aspect, the invention features a multispectral illuminator for providing EM radiation with a selectable frequency content. The multispectral illuminator includes: a dispersive element which during operation provides an angular dispersion for incident EM radiation; a light source array including an array of light sources providing EM radiation at different wavelengths; and an optical system having an optical power. The optical system is positioned relative to the source array and the dispersive element to image the dispersive element at infinity with respect to the light source array for at least one of the different wavelengths in a paraxial approximation. The position of each light source along the array and the angular dispersion of the dispersive element are selected to cause at least a portion of the EM radiation from the source array incident on the dispersive element through the optical system to propagate along a common direction.

Embodiments of the multispectral illuminator may include any of the following features.

The optical system can include any of a singlet lens, a composite lens system, and one or more curved reflective surfaces.

During operation, the optical system may collimate the EM radiation emerging from each light source within a preset cone angle and direct the collimated radiation from each light source to be coextensive on the diffractive element.

The optical system can define a focal length for at least one of the different wavelengths, and the light source array and the diffractive element can be each spaced from the optical system by a distance substantially equal to the focal length.

The spatial extent of the dispersive element can define an aperture stop for the optical system. For example, the dispersive element can include an iris for varying the spatial extent of the dispersive element.

The optical system and the dispersive element can cause the EM radiation propagating along the common direction to have a spatial distribution that is substantially wavelength independent.

The common direction can be substantially collinear with a chief ray from a central one of the light sources.

The dispersive element can be a reflective dispersive element (e.g., a reflective grating). For example, the reflective dispersive element can direct the radiation back to the optical system along the common direction, and the optical system can focus the radiation received from the reflective dispersive element to a spot in an image field. The image field may be substantially coplanar with a plane defined by the source array. Also, the common direction may be substantially perpendicular to a plane defined by the source array. The source array may include a substrate supporting the light sources, and the spot in the image field may coincide with an aperture in the substrate. The light sources may extend along an axis, and the aperture can lie along the light source axis. Alternatively, the aperture can lie above or below the light source axis. The optical system may form a telecentric imaging system based on the reflection by the dispersive element. The multispectral illuminator may further include an optical fiber positioned to receive the focused radiation from the aperture in the substrate.

Alternatively, the dispersive element may be a transmissive dispersive element (e.g., a transmission grating). The multispectral illuminator may further include a second optical system position to receive the radiation from the transmissive dispersive element propagating along the common direction and focus that radiation to a spot in an image field. The common direction may be substantially perpendicular to a plane defined by the source array. The two optical systems may form a telecentric imaging system.

The second optical system may define a focal length, and the transmissive dispersive element and the image field can be each spaced from the second optical system by a distance substantially equal to the focal length of the second optical system. The multispectral illuminator may further include an optical fiber positioned to receive the focused radiation from the spot in the image field.

The multispectral illuminator can further include an electronic controller coupled to the array of light source for selectively adjusting the EM radiation provided by each light source.

The EM radiation provided by the array of light sources may span wavelengths within the range of 400 nm to 1000 nm.

The source array may includes a substrate supporting the light sources, and each light source may include at least one light emitting diode (LED) mounted on the substrate. For example, each light source may include multiple light emitting diodes (LED) mounted on the substrate.

The source array may include a substrate supporting the light sources, and the substrate may further support a reflective cup surrounding each light source to enhance light emission from the light sources in a forward direction.

The light source array may further include a lenslet array aligned with the array of light sources.

The source array can support at least two of the light sources at different axial positions relative to the optical system to reduce at least one of field curvature and axial chromatic aberration in the collimated EM radiation incident on the dispersive element. For example, the substrate can have curved surface supporting the light sources to provide the different axial positions.

Furthermore, the source array can support at least two of the light sources at lateral positions along the array that reduce at least one of distortion and lateral chromatic aberration in the collimated EM radiation incident on the dispersive element. For example, the substrate can support the light sources at lateral positions along the array that vary nonlinearly with the central frequency of the EM radiation provided by each light source.

The multispectral illuminator may further include beam modification optics positioned to receive light derived the EM radiation propagating along the common direction and produce an illumination pattern having a desired spot size and a desired divergence cone across the spot size. The beam modification optics may include a diffuser (e.g., a holographic diffuser) for modifying the divergence of an incident beam. Moreover, the beam modification optics may include multiple diffusers each providing a different scattering cone, where each of the multiple diffusers can be selectably positioned to intercept the light derived from the EM radiation propagating along the common direction. The beam modification optics can further include at least one lens. Moreover, the beam modification optics may further include multiple lenses having different focal lengths, where each of the multiple lenses can be selectably positioned to intercept the light derived from the EM radiation propagating along the common direction.

The multispectral illuminator may further include a detector positioned to receive a monitoring beam derived from a portion the EM radiation propagating along the common direction.

The multispectral illuminator may further include a multi-channel detector positioned to receive an array of monitoring beams derived from the EM radiation provided by the source array, wherein each monitoring beam corresponds to one of the light sources. In some embodiments, the multi-channel detector can be positioned above or below the array of sources. For example, a substrate in the source array can further support the multi-channel detector.

To produce the monitoring beams, the multispectral illuminator may include a monitoring beam optic positioned between the source array and the optical system for producing the monitoring beams from corresponding portions of the EM radiation provided by the light sources. For example, the monitoring beam optic can include a partially transparent roof mirror extending parallel to the array of light sources.

In other embodiments, the dispersive element can cause a first portion of the incident EM radiation from the light sources to propagate along the common direction and cause a second portion of the incident EM radiation to form the monitoring beams. For example, the dispersive element may reflect or transmit the second portion to form the monitoring beams.

Furthermore, the dispersive element may diffract the first portion to cause it to propagate along the common direction and diffract the second portion along an order different from that of the first portion to form the monitoring beams. The monitoring beams produced by the dispersive element may propagate through the optical system prior to being received by the multi-channel detector.

In yet further embodiments, the multispectral illuminator includes a monitoring beam optic positioned between the optical system and the dispersive element to produce the monitoring beams from a portion of the EM radiation being imaged by the optical system. The monitoring beams may propagate through the optical system prior to being received by the multi-channel detector. For example, the monitoring beam optic may be a wedge positioned immediately adjacent the dispersive element.

The multispectral illuminator may be part of a spectral imaging system that further includes: beam delivery optics positioned to form an illumination pattern on a sample based on the EM radiation produced by the multispectral illuminator; an detection optics (e.g., a lens) positioned to receive light from the sample in response to the illumination pattern and form an image of the sample in a focal plane; and an imaging detector located in the focal plane for detecting and spatially resolving the image of the sample.

The beam delivery optics in the spectral imaging system may include a diffuser (e.g., a holographic diffuser) for controlling the divergence of an incident beam. Moreover, the beam delivery optics may include multiple diffusers each providing a different scattering cone, and each of the multiple diffusers can be selectably positioned to intercept EM radiation used to form the illumination pattern. Also, the beam delivery optics may further include at least one lens. Moreover, the beam delivery optics may further include multiple lenses having different focal lengths, and each of the multiple lenses can be selectably positioned to intercept the light derived from the EM radiation used to form the illumination pattern. The detection optics collect light within a numerical aperture, and the beam delivery optics may be selected to cause the EM radiation in the illumination pattern incident on the sample to fill the numerical aperture of the detection optics. Furthermore, the detection optics collect light from the sample over a sample area for light rays emerging from the sample area within the numerical aperture, and the beam delivery optics may be selected to cause the illumination pattern to fill the sample area and the numerical aperture.

In general, in another aspect, the invention features a multispectral illuminator for providing EM radiation with a selectable frequency content. The multispectral illuminator includes: a dispersive element which during operation provides an angular dispersion for incident EM radiation; a light source array including an array of light sources providing EM radiation at different wavelengths; and an optical system having an optical power. During operation, the optical system collimates the EM radiation emerging from each light source within a preset cone angle and directs the collimated radiation from each light source to be coextensive on the diffractive element, and the position of each light source along the array and the angular dispersion of the dispersive element are selected to cause at least a portion of the EM radiation from the source array incident on the dispersive element through the optical system to propagate along a common direction.

In general, in another aspect, the invention features a multispectral illuminator for providing EM radiation with a selectable frequency content. The multispectral illuminator includes: a dispersive element which during operation provides an angular dispersion for incident EM radiation; a light source array including an array of light sources providing EM radiation at different wavelengths; and an optical system having an optical power. The optical system defines a focal length for at least one of the different wavelengths, the light source array and the diffractive element are each spaced from the optical system by a distance substantially equal to the focal length, and the position of each light source along the array and the angular dispersion of the dispersive element are selected to cause at least a portion of the EM radiation from the source array incident on the dispersive element through the optical system to propagate along a common direction.

In general, in another aspect, the invention features a multispectral illuminator for providing EM radiation with a selectable frequency content. The multispectral illuminator includes: a dispersive element which during operation provides an angular dispersion for incident EM radiation; a light source array including a substrate supporting an array of light sources providing EM radiation at different wavelengths; and an optical system having an optical power. The optical system is positioned to direct light from the light source array to the dispersive element, and the position of each light source along the array and the angular dispersion of the dispersive element are selected to cause EM radiation from the source array incident on the diffractive element through the optical system to propagate along a common direction. The substrate supports at least two of the light sources at different axial positions relative to the optical system to reduce at least one of field curvature and axial chromatic aberration in the collimated EM radiation incident on the dispersive element.

In general, in another aspect, the invention features a multispectral illuminator for providing EM radiation with a selectable frequency content. The multispectral illuminator includes: a dispersive element which during operation provides an angular dispersion for incident EM radiation; a light source array including an array of light sources providing EM radiation at different wavelengths; an optical system having an optical power, and a multi-channel detector positioned to receive an array of monitoring beams derived from the EM radiation provided by the source array. The optical system is positioned to direct light from the light source array to the dispersive element. Each monitoring beam corresponds to one of the light sources. The position of each light source along the array and the angular dispersion of the dispersive element are selected to cause EM radiation from the source array incident on the diffractive element through the optical system to propagate along a common direction.

Embodiments of the multispectral illuminator may include any of the following features.

The multi-channel detector may be positioned above or below the array of sources. For example, a substrate in the source array can support the multi-channel detector.

To produce the monitoring beams, the multispectral illuminator may further include a monitoring beam optic positioned between the source array and the optical system for producing the monitoring beams from corresponding portions of the EM radiation provided by the light sources.

In other embodiments, the dispersive element may cause the first portion of the incident EM radiation from the light sources to propagate along the common direction, and cause a second portion of the incident EM radiation to form the monitoring beams. For example, the dispersive element may reflect or transmit the second portion to form the monitoring beams. Furthermore, the dispersive element may diffract the first portion to cause it to propagate along the common direction, and diffract the second portion along an order different from that of the first portion to form the monitoring beams. The monitoring beams may then propagate through the optical system prior to being received by the multi-channel detector.

In yet further embodiments, the multispectral illuminator may further include a monitoring beam optic positioned between the optical system and the dispersive element to produce the monitoring beams from a portion of the EM radiation being directed by the optical system. The monitoring beams may then propagate through the optical system prior to being received by the multi-channel detector. The monitoring beam optic may be a wedge positioned immediately adjacent the dispersive element. The multi-channel detector may then be positioned above or below the array of sources, and the optical system directs the monitoring beams from the monitoring beam optic to form an image of the source array on the multi-channel detector. A substrate in the source array may be used to support the multi-channel detector.

The multispectral illuminator may also be part of a spectral imaging system that further includes: beam delivery optics positioned to form an illumination pattern on a sample based on the EM radiation produced by the multispectral illuminator; detection optics position to receive light from the sample in response to the illumination pattern and form an image of the sample in a focal plane; and an imaging detector located in the focal plane for detecting and spatially resolving the image of the sample.

In general, in another aspect, the invention features a spectral imaging system including: a multispectral illuminator producing EM radiation, the illuminator including an array of sources at different wavelengths; beam modification optics positioned to form an illumination pattern on a sample based on the EM radiation produced by the multispectral illuminator; detection optics (e.g., a lens) positioned to receive light from the sample in response to the illumination pattern and form an image of the sample in a focal plane; and an imaging detector located in the focal plane for detecting and spatially resolving the image of the sample. The illumination pattern formed by the beam modification optics produce a desired spot size and a desired divergence cone across the spot size. The beam modification optics include a diffuser (e.g., a holographic diffuser) for controlling at least one of the spot size and divergence cone of the illumination pattern.

Embodiments of the spectral imaging system may include any of the following features.

The EM radiation produced by the multispectral illuminator may have a substantially spectrally uniform spatial profile.

The beam modification optics may include multiple diffusers each providing a different scattering cone and wherein each of the multiple diffusers can be selectably positioned to intercept EM radiation used to form the illumination pattern.

The beam modification optics may further include at least one lens. Furthermore, the beam modification optics further include multiple lenses having different focal lengths and each of the multiple lenses can be selectably positioned to intercept the light derived from the EM radiation used to form the illumination pattern.

The detection optics collect light within a numerical aperture, and the beam delivery optics may be selected to cause the EM radiation in the illumination pattern incident on the sample to fill the numerical aperture of the detection optics. Furthermore, the detection optics collect light from the sample over a sample area for light rays emerging from the sample area within the numerical aperture, and the beam delivery optics may be selected cause the illumination pattern to fill the sample area and the numerical aperture.

Other features, objects, and advantages of the invention will be apparent from the following detailed description.

DESCRIPTION OF DRAWINGS

The invention will now be further described merely by way of example with reference to the accompanying drawings.

FIG. 7a is a plan view of source array 210 and detector array 790. FIG. 7b is a side view of one embodiment of multispectral illuminator 200 that use monitoring optic 292. FIG. 7c is a side view of another embodiment of multispectral illuminator 200 that use monitoring optic 294.

Like reference symbols in the various drawings indicate like elements.

DETAILED DESCRIPTION

Figure 1:
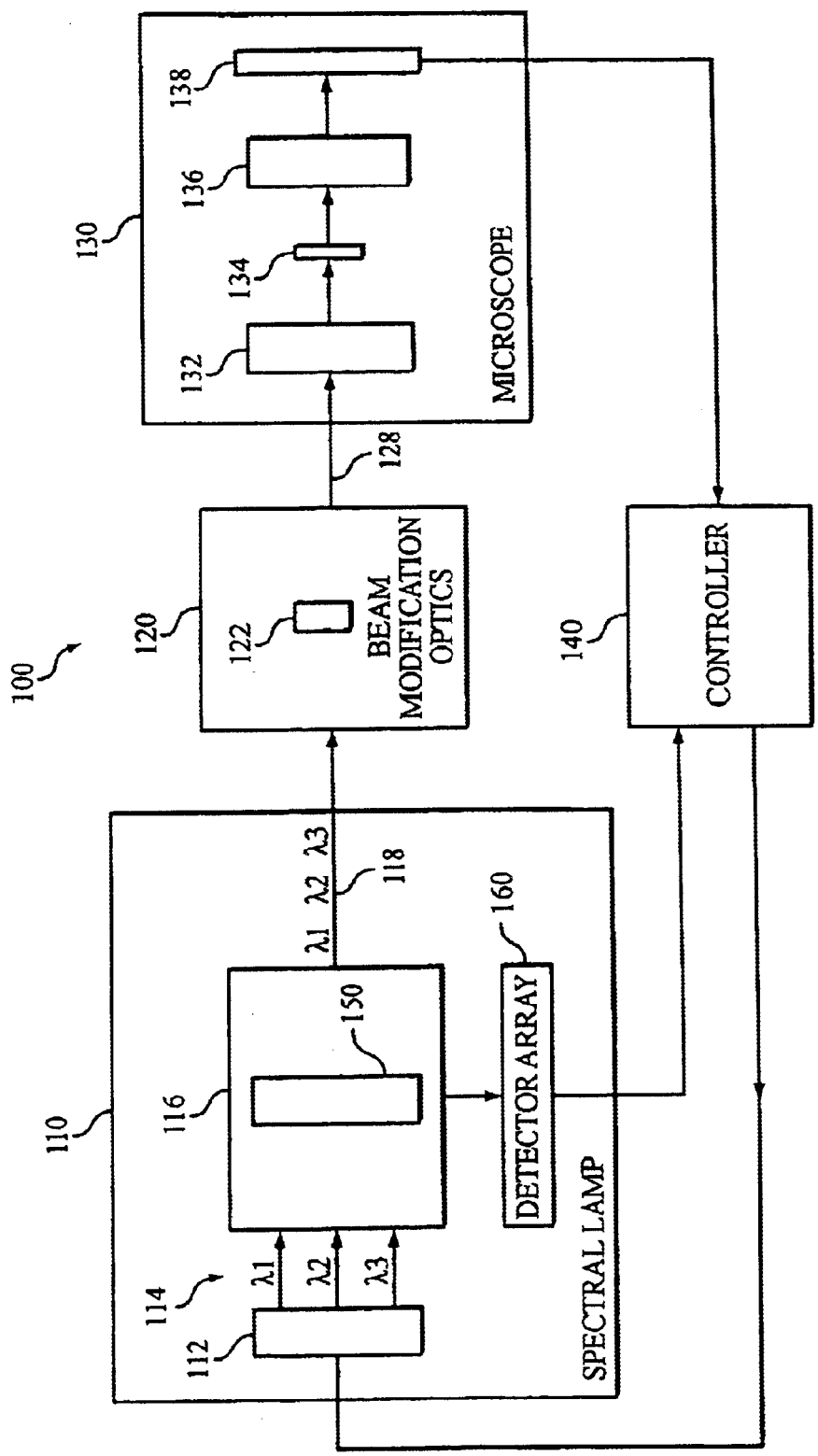
FIG. 1 is a schematic diagram of a multispectral microscopy system 100.

Referring to FIG. 1, the invention features a multispectral microscopy system 100, which includes a multispectral illuminator 110, beam modification optics 120, a microscope 130, and an electronic controller 140. These components are first discussed briefly and then particular components are described in greater detail further below and with reference to subsequent figures.

Multispectral illuminator 110 includes an extended light source array 112 providing multiple sources of electromagnetic (EM) radiation 114 at different wavelengths ($\lambda_1$, $\lambda_2$, $\lambda_3$ . . . ) from different positions along the extended array. Multispectral illuminator 110 further includes multispectral illuminator optics 116 that receive EM radiation 114 at the different wavelengths and combines them to produce an output beam 118. In preferred embodiments of illuminator 110, output beam 118 has a spectral content that is substantially uniform across the transverse spatial profile of beam. As described subsequently, such uniformity can be accomplished through proper positioning of the optics in the illuminator. Furthermore, even where there is some deviation from such proper positioning, a scrambling optic, such as a sufficient length of optical fiber can be used to homogenize the spectral profile of the output beam across its spatial profile and achieve the substantially uniform spectral content. Controller 140 is coupled to light source array 112 to independently control the intensity output of each light source, and thereby select the spectral content of output beam 118. Multispectral illuminator 110 further includes monitoring optics 150 and a monitoring detector 160 coupled to controller 140. Monitoring optics 150 sample the output of the EM radiation from the light source array and directs it to detector 160, which monitors the output and provides calibration, feedback, and/or source aging information to controller 140.

Beam modification optics 120 are positioned to receive output beam 118 and modify its spot size and divergence cone to produce modified output beam 128. In preferred embodiments, the beam modification optics include a diffuser 122 (e.g., holographic diffuser) and one or more lenses to independently modify the divergence cone and the spot size of output beam 128. The modifications imparted by beam modification optics 120 are selected to optimize the light efficiency, field of view, and resolution of microscope 130, which uses the modified output beam to provide an excitation illumination pattern on a sample 134. Furthermore, the beam modification optics may include multiple diffusers each having a different scattering cone, wherein each of the multiple diffusers may be selectively positioned in the beam path to alter the beam modification. Similarly, the beam modification optics may include multiple lenses each having a different focal length, wherein each of the multiple lenses may be selectively positioned in the beam path to alter the beam modification. Such alteration be useful to accommodate changes in the microscope magnification and/or sample size.

Microscope 130 includes source optics 132 that receive the modified output beam and form the illumination pattern on sample 134. Microscope 130 further includes detection optics 136 that collect light emerging from the sample in response to the illumination pattern and image it onto detector 138, which spatially resolves the light to record an image of the sample. Detector 138 sends the image information to controller 140 for storage and/or analysis. The light emerging from the sample can be, for example, transmitted or partially transmitted light from the illumination pattern, in which case the detector measures absorption by the sample. In other applications, the emerging light from the sample can be fluorescence and/or scattered light from the sample in response to the illumination pattern. In any case, the image recorded by detector 138 is a multispectral image providing the sample's response to a multispectral illumination pattern, whose spectral content is selectable through the controller's connection to the source array in multispectral illuminator 110. Suitable optics for source optics 132 and detection optics 136 include those commonly found in microscopes and are well-known in the art. Detector 138 independently records light intensity at multiple points along a grid, which may extend along one or two dimensions. Suitable detectors include charge-coupled device (CCD) detectors, complementary metal oxide semiconductors (CMOS) detectors, charge-injection device (CID) detectors, vidicon detectors, reticon detectors, image-intensifier tube detectors, and pixelated photomultiplier tube (PMT) detectors.

Depending on the embodiment, the microscope may be configured for use in a work station (e.g., for analyzing in vitro biological samples), or for use in an endoscope or retinal scanner for in vivo applications. In additional embodiments, the output beam from the multispectral illuminator (and/or the modified output beam from the multispectral illuminator and the beam modification optics) can be used in other downstream applications besides that of a microscope. For example, the illuminator may also be useful in macroscopic imaging in which there is no magnification or even demagnification of a sample field. For example, the multispectral illuminator may be used to analyze whether objects are counterfeit. The illuminator may also be utilized in microscope (or macroscope) that is incorporated into an endoscope or any other in vivo imaging tool.

Controller 140 includes the electronic interface and drive circuitry necessary to control the output of light source array 112 and to receive information from the monitoring detector 160 and microscope detector 138. Controller 140 also includes a processor and input/output devices (e.g., keyboard, monitor, printer, etc.) necessary to run experimental routines that exploit the multi-spectral control of system 100, calibrate the output of multispectral illuminator 110, and/or provide servo-control over the output of multispectral illuminator 110.

Figure 2A:
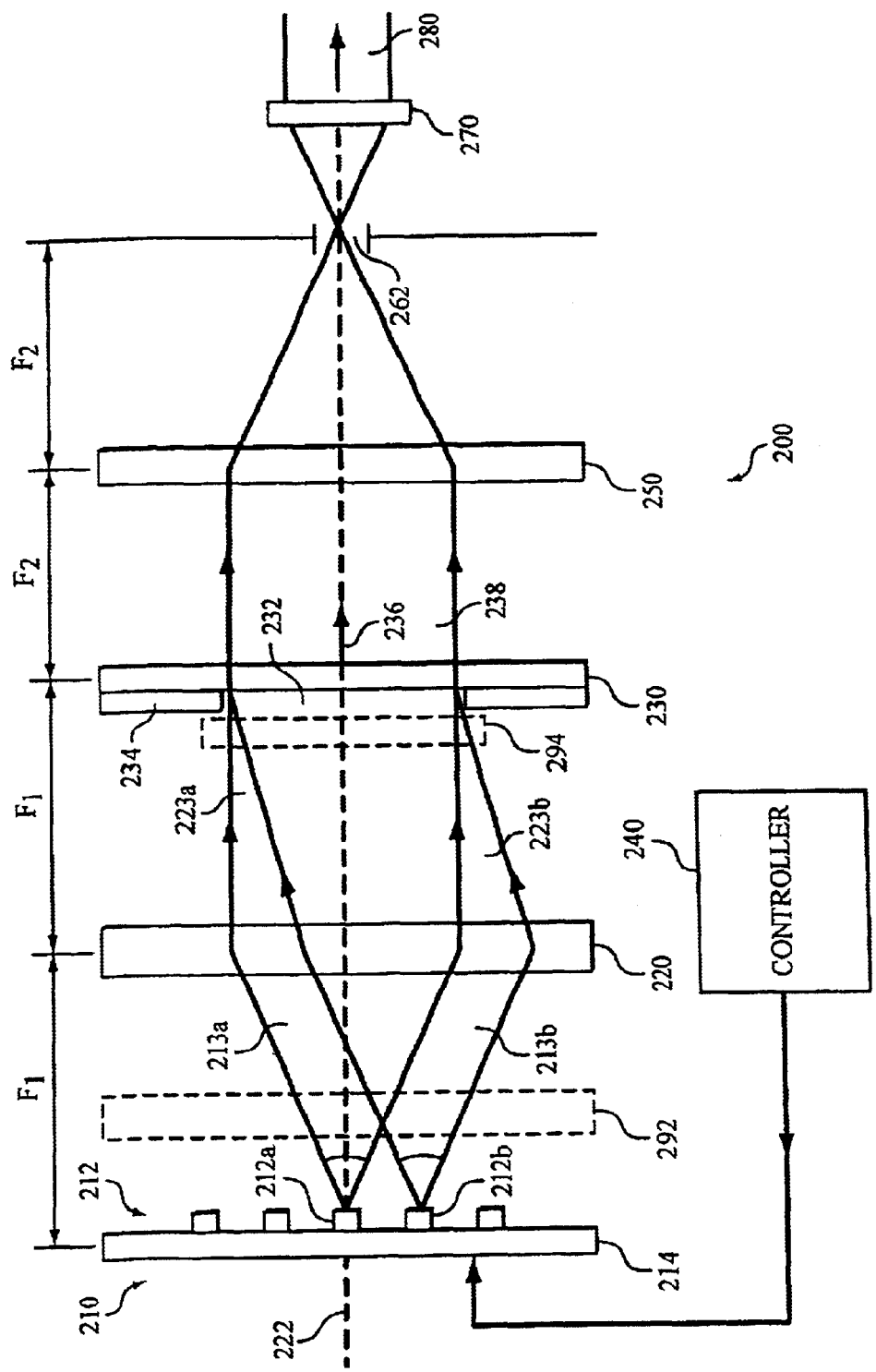
FIG. 2a is a schematic diagram of a multispectral illuminator 200.

Referring now to FIG. 2a, a particular embodiment of a multispectral illuminator 200 is shown. Multispectral illuminator 200 includes a source array 210 formed by an array of light emitting diodes (LEDs) 212 supported along a substrate 214. Each diode is selected to emit EM radiation at a particular wavelength band and defines a source in the array for that wavelength band. For example, LEDs 212a and 212b provide radiation cones 213a and 213b at wavelengths $\lambda_A$ and $\lambda_B$, respectively, where for simplicity we specifically label the output of only two of the diodes. An electronic controller 240 coupled to the source array controls the input current to each diode, and thereby, the output intensity output of each diode.

Multispectral illuminator 200 further includes a transmission grating 230 and a first lens 220 having a focal length $F_1$. Source array 210 and transmission grating 230 are positioned in the front and back focal planes, respectively, of lens 220. As a result, lens 220 collimates the radiation cone from each point of each LED source in source array 210. Referring to FIG. 2a, for example, lens 220 produces collimated radiation 223a and 223b corresponding to LED sources 212a and 212b, respectively, where we treat sources 212a and 212b as point sources. Moreover, lens 220 directs the collimated radiation from each point of each LED source to be coextensive on an active area 232 of transmission grating 230. In other words, the EM radiation from each LED source overlaps entirely with one another on the active area of the grating.

Grating 230 further includes an opaque region surrounding active area 232 to define a field stop 234. Alternatively, a separate field stop can be positioned adjacent the grating to surround the active area. In either case, the grating and stop define the aperture stop for the light collect by lens 220 of the radiation emerging from the LEDs sources.

Transmission grating 230 is selected to cause the EM radiation from each LED source that is coextensive on active area 232 to diffract along a common direction 236 and produce output radiation 238. In the embodiment of FIG. 2a, common direction 236 is collinear with the optical axis 222 of lens 220, and also collinear with the chief ray in radiation cone 213a from LED 212a, which is the middle one of the LED sources in source array 210. To cause the EM radiation from each LED source to diffract along the common direction, the angular dispersion in the radiation incident on the grating is matched to the angular dispersion of the grating.

Figure 2B:
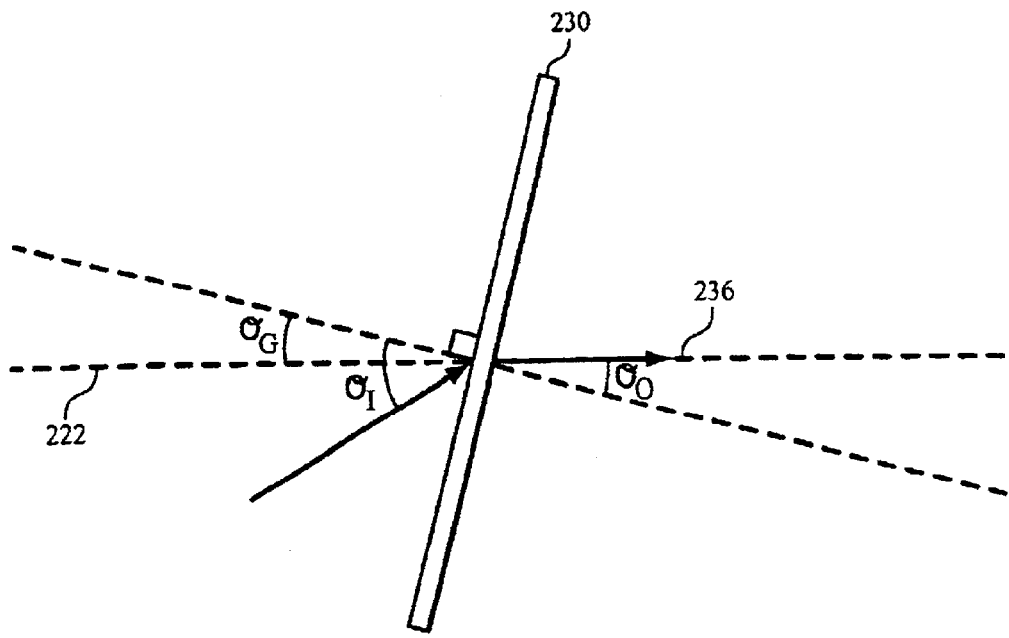
FIG. 2b is a diagram showing the angles of incidence and diffraction for radiation interacting with a grating 230 in multispectral illuminator 200.

Referring to FIG. 2b, the angular dispersion of the incident radiation depends on the lateral displacement of the different wavelength sources along source array 210. If $X(\lambda_n)$ gives the lateral displacement of the LED source corresponding to wavelength $\lambda_n$ from the position of the middle LED source (which is shown in FIG. 2a) and $\theta_G$ gives the orientation grating 230 as defined by the angle between the grating normal and optical axis 222, the incident angle $\theta_1(\lambda_n)$ on grating 230 of the radiation corresponding to wavelength $\lambda_n$ is given by:

$$\theta_1(\lambda_n) = \tan\ [X(\lambda_n)/F_1] - \theta_G \qquad (1),$$

which in the paraxial approximation gives:

$$\theta_1(\lambda_n) \approx X(\lambda_n)/F_1 - \theta_G \qquad (2),$$

The output angle $\theta_D$ relative to the grating normal of the radiation diffracted by the grating ("the diffracted angle") is given by the usual grating equation:

$$\sin\ \theta_D = m\lambda_n/d + \sin\ \theta_1(\lambda_n) \qquad (3),$$

where d gives the grating line spacing and m is the diffraction order. Accordingly, to match the angular dispersions, the lateral displacement of the LED sources $X(\lambda_n)$ and the grating properties (grating orientation $\theta_G$, grating line spacing d, and diffraction order m) are selected to make the output angle $\theta_D$ the same for each of the wavelengths $\lambda_n$ according to the equations above. Inspection of the equations shows that the lateral displacement $X(\lambda_n)$ of the LED sources should either increase or decrease with wavelength. Furthermore, to have common direction 236 collinear with optical axis 222, one chooses the parameters to give $\theta_D = \theta_G$.

Referring again to FIG. 2a, multispectral illuminator 210 further includes a second lens 250 having a focal length $F_2$ and a pinhole 262, where grating 230 and pinhole 262 are positioned in the front and back focal planes of lens 250, respectively. Lenses 220 and 250 define an imaging system that images the LED sources in source array 210 to pinhole 262 in a corresponding image plane. The presence of grating 230 causes the images of each LED source to overlap and be coextensive on pinhole 262 and to propagate collinearly through pinhole 262. Output radiation that emerges from pinhole 262 can be collimated by a collimating lens 270 to produce an output beam 280. Because the images of each LED source overlap and are coextensive on pinhole 262 and because the images propagate collinearly through pinhole 262, the spectral content of output beam 280 is substantially uniform across its transverse profile. Moreover, controller 240 can electronically select that spectral content based on independent drive signals to the respective LED sources 212.

In additional embodiments, the output radiation that emerges from pinhole 262 can be collected by an optical fiber, which may be used to couple the output radiation to another location. The optical fiber may further homogenize the beam to insure that its spectral content is substantially uniform across its spatial profile. The optical fiber functions to make the rays from each source element collinear.

Multispectral illuminator 200 may further include monitoring optics positioned between source array 210 and first lens 220 (as indicated by dashed box 292) or between first lens 220 and grating 230 (as indicated by dashed box 294). The monitoring optics sample the output from LED sources 212 to produce a corresponding array of monitor beams and direct them to a detector array coupled to the controller 240. The detector array measures the intensity of the monitor beams to independently monitor the performance of each LED source. Specific embodiments for the monitoring optics are described in greater detail further below.

Multispectral illuminator 200 of FIG. 2a involves the use of a transmission grating. In other embodiments, a reflection grating can be used, resulting in a folded arrangement, which may be preferable because of a reduction in optics. Such an arrangement is shown with reference to FIGS. 3a and 3b as multispectral illuminator 300. Multispectral illuminator 300 includes components common to multispectral illuminator 200 and operates similarly. Such an embodiment is described in detail below Referring to FIG. 3a, multispectral illuminator 300 includes a source array 310 formed by an array of light emitting diodes (LEDs) 312 supported along a substrate 314. Each diode is selected to emit EM radiation at a particular wavelength band and defines a source for that wavelength band. For example, LEDs 312a and 312b provide radiation cones 313a and 313b at wavelengths $\lambda_A$ and $\lambda_B$, respectively, where for simplicity we specifically label the output of only two of the diodes. An electronic controller 340 coupled to the source array controls the input current to each diode, and thereby, the output intensity output of each diode.

Figure 3B:
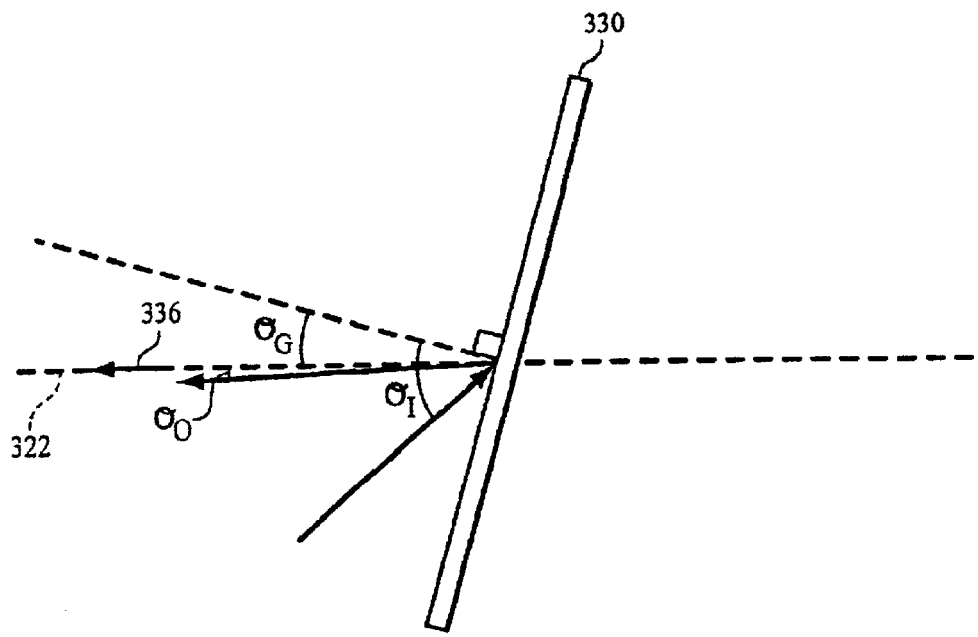
FIG. 3b is a diagram showing the angles of incidence and diffraction for radiation interacting with a grating 330 in multispectral illuminator 300.
Figure 3A:
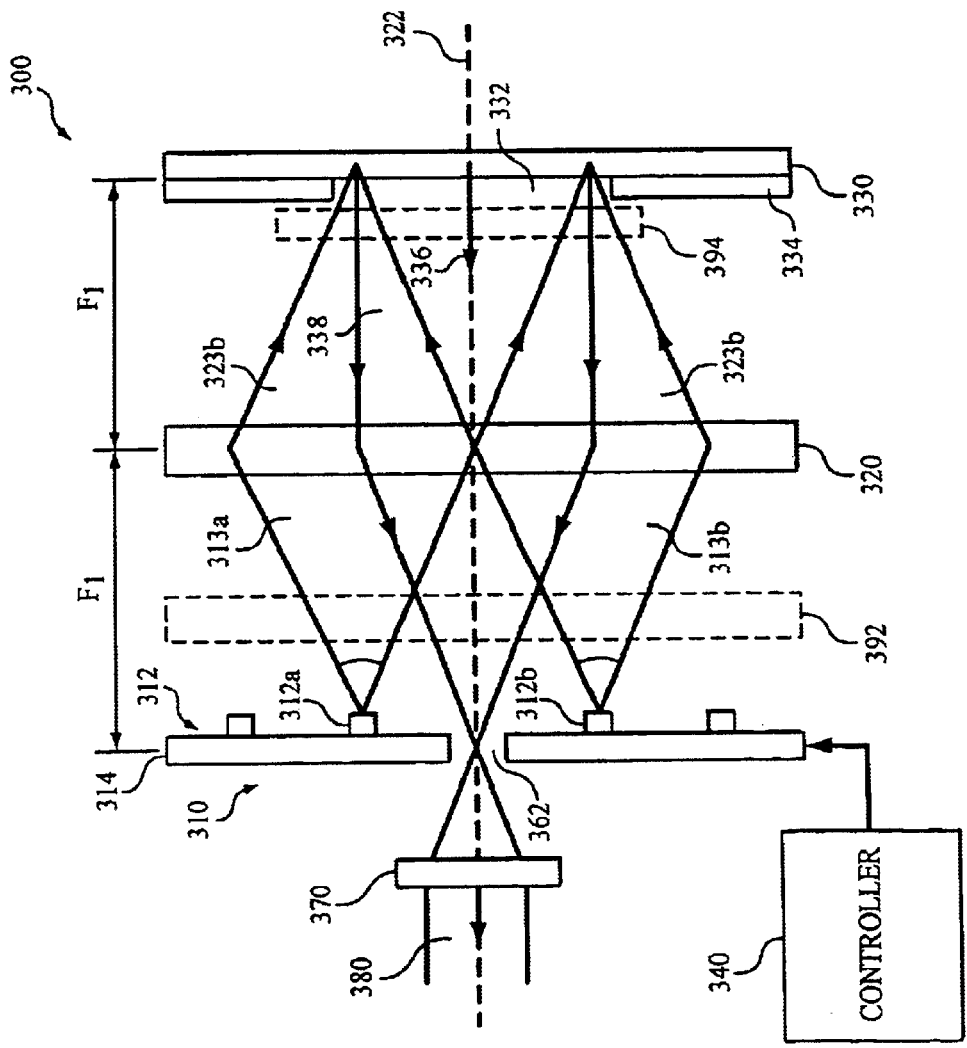
FIG. 3a is a schematic diagram of another multispectral illuminator 300.

Multispectral illuminator 300 further includes a reflection grating 330 and a first lens 320 having a focal length $F_1$. Source array 310 and reflection grating 330 are positioned in the front and back focal planes, respectively, of lens 320. As a result, lens 320 collimates the radiation cone from each point of each LED source in source array 310. Referring to FIG. 3a, for example, lens 320 produces collimated radiation 323a and 323b corresponding to LED sources 312a and 312b, respectively, where we treat sources 312a and 312b as point sources. Moreover, lens 320 directs the collimated radiation from each point of each LED source to be coextensive on an active area 332 of reflection grating 330. In other words, the EM radiation from each LED source overlaps entirely with one another on the active area of the grating. Grating 330 further includes an opaque (light-absorbing) region surrounding active area 332 to define a field stop 334. Alternatively, a separate field stop can be positioned adjacent the grating to surround the active area. In either case, the grating and stop define the aperture stop for the light collect by lens 220 of the radiation emerging from the LEDs sources.

Reflection grating 330 is selected to cause the EM radiation from each LED source that is coextensive on active area 332 to diffract along a common direction 336 to define output radiation 338. Like the embodiment of FIG. 2a, common direction 336 is collinear with the optical axis 322 of lens 320. However, common direction 336 points back to source array 310 and output radiation 338 propagates towards lens 320 and source array 310 to form a folded optical system. To cause the EM radiation from each LED source to diffract along the common direction, the angular dispersion in the radiation incident on the grating is matched to the angular dispersion of the grating. This is accomplished in the same way as described above for the unfolded arrangement of FIG. 2a, except that the output angle $\theta_D$ and incident angle $\theta_1(\lambda_n)$ now refer to the same side of the grating as shown in FIG. 3b.

Referring again to FIG. 3a, following reflection grating 330, output radiation 338 is focused by lens 320 onto a pinhole in 362 in source array 310. Thus, lens 320 and reflection grating 330 define a folded, double-pass imaging system that images the LED sources in source array 310 to pinhole 362 in a corresponding image plane substantially coplanar with source array 310. The presence of grating 330 causes the images of the LED sources to overlap and be coextensive on pinhole 362, and to propagate collinearly through pinhole 362. Output radiation that emerges from pinhole 362 can be collimated by a collimating lens 370 to produce an output beam 380. Because the images of the LED sources overlap and are coextensive on pinhole 362 and propagate collinearly through it, the spectral content of output beam 380 is substantially uniform across its transverse profile. Moreover, controller 340 can electronically select that spectral content based on independent drive signals to the respective LED sources 312.

In additional embodiments, the output radiation that emerges from pinhole 362 can be collected by an optical fiber, which may be used to coupled the output radiation to another location. The optical fiber may further homogenize the beam to insure that its spectral content is substantially uniform across its spatial profile. The optical fiber functions to make the rays from each source element collinear.

Pinhole 362 in source array 310 may be positioned along a common axis with LED sources 312 as shown in FIG. 3a. Alternatively, pinhole 362 may be positioned above or below an axis defined by the LED sources to prevent any reduction in the maximum LED density along the array axis. In such embodiments, reflection grating 330 is tilted out of the plane of FIG. 3a to direct output radiation 338 to pinhole 362.

Like the embodiment of FIG. 2a, multispectral illuminator 300 may further include monitoring optics positioned between source array 310 and first lens 320 or between first lens 320 and grating 330, and a detector array positioned to receive monitor beams produced by the monitoring optics. Specific embodiments for the monitoring optics are described in greater detail further below.

In further embodiments, any of the lenses described above can be replaced with a generalize optical system having optical power. Such systems may include one or more lenses and/or curved mirrors. For example, the generalize optical system may include multiple components each having optical power, e.g., it may be doublet lens or a triple lens.

In the limit that such optical system defines a unique focal length F, as we have assumed in the embodiments described above, the source array and the grating are positioned in the front and back focal planes of the optical system. As a result, the optical system images the grating at infinity with respect to each source element of the light source array, and thus each source element sees the same region of the grating and the light from each element is coextensive on that region. The grating can then produce output radiation whose spectral content is substantially uniform across its transverse profile by compensating for the dispersion associated with lateral position of the different wavelength band sources. Moreover, this allows the spectral content of the output beam from the multispectral illuminator to be substantially uniform across its transverse profile. In practice, however, it may be difficult to precisely define a unique focal length for the optical system because of various aberrations. For example, the optical system may focus rays to slightly different positions according to their wavelength or their lateral position on the source object.

In additional embodiments, therefore, the relative positions of the optical system, the source array, and the grating are selected according to the more general condition that the optical system images the grating at infinity with respect to each source element of the light source array, at least for paraxial rays that emerge from each source. Note that for a ray propagating at an angle θ to the optical axis, a paraxial ray has sin θ≈θ. This "infinity" condition can be achieved by positioning each source element at a nominal back focal plane of the optical system to within the depth of field of the optical system, and positioning the grating at nominal front focal plane of the optical system to within the depth of field of the optical system. The depth of field (DOV) is related to the numerical aperture (NA) of the optical system according to DOV=λ/NA$^2$, where λ is the wavelength of the light from the source element.

Moreover, the optical system may be designed with multiple components to provide multiple degrees of freedom to compensate for various optical aberrations (e.g., field curvature, axial chromatic, lateral chromatic, distortion, and coma). Although additional components in the optical system provide additional degrees of freedom for reducing aberrations, each additional component also adds cost and complexity to the optical system. Therefore, preferred embodiments may include only a handful of components in the optical system. In any case, the design of suitable optical systems can be determined standard ray tracing techniques and lens design software well known in the art. For example, suitable software includes: CODE V by Optical Research Associates; ZEMAX by Focus Software, Inc.; OSLO by Lambda Research Corporation; SIGMA-2000 by Kidger Optics Ltd.; Roadrunner by Acme Optics; and SYNOPSYS by Breault Research Organization. When using such software, a suitable proxy for determining when the optical system images the grating at infinity with respect to each source element, is to optimize the overlap in position and propagation direction of the chief rays from the source array as they emerge from the grating. Note that the chief ray(s) for a given source element are defined as the rays that pass through the center of the aperture stop for the system, which corresponds to the active area of the grating in the embodiments above.

Figure 4A:
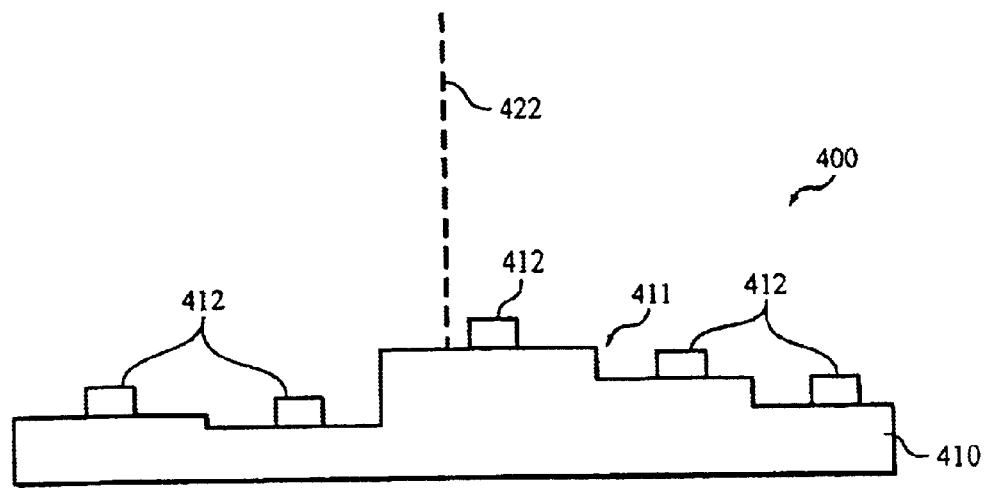
FIG. 4a is a schematic diagram of a source array 400 that varies the axial position of its source elements.
Figure 4B:
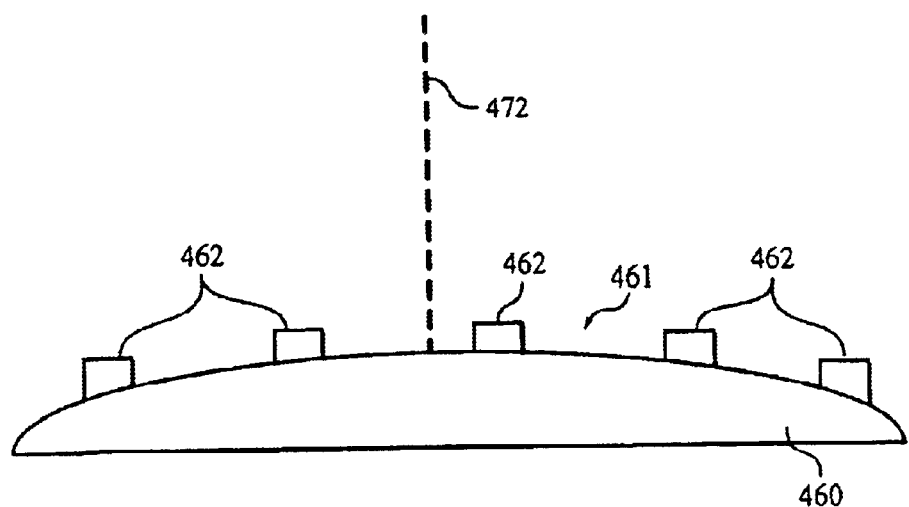
FIG. 4b is a schematic diagram of another source array 450 that varies the axial position of its source elements.

To further provide additional degrees of freedom in the optical design, the substrate that supports the different source elements in the source array can be designed to introduce small axial displacements among the source elements. Referring to FIG. 4a, for example, a source array 400 includes a substrate 410 supporting multiple source elements 412 along a stepped surface 411. The stepped surface introduces small displacements in the axial position of each source element 412 relative to the optical axis 422 of the generalized optical system. The displacements can be selected to reduce field curvature and axial chromatic aberration in the output of the multispectral illuminator caused by the optical system. The stepped surfaces can also accommodate variations in the axial thicknesses of the source elements themselves. In another embodiment, shown in FIG. 4b, a source array 450 includes a substrate 460 supporting multiple source elements 462 along a curved surface 461. Like the embodiment of FIG. 4a, the curved surface introduces small displacements in the axial position of each source element 462 relative to the optical axis 472 of the generalized optical system. Here, the curvature of the surface 461 can be selected to reduce field curvature and axial chromatic aberration in the output of the multispectral illuminator caused by the optical system. Of course, in additional embodiments, a step-height displacements can also be introduced to the curved substrate. Furthermore, although the grating equation (e.g., Eq. 3 above) is typically used to guide the nominal lateral placement of the different-wavelength source elements along the source array, such lateral placements can be adjusted to reduce distortion and lateral chromatic aberration caused by the generalized optical system.

In preferred embodiments, the source array, the grating, and the generalized optical system positioned there between define a telecentric imaging system. Such a system is produced when the chief ray(s) from each source element emerges perpendicular to the source array, where the chief ray for a given source element is defined as the rays that pass through the center of the aperture stop for the system. Notably, multispectral illuminators 200 and 300 shown in FIGS. 2a and 2b, respectively, are telecentric systems. Such systems tend to produce smaller optical aberrations. Furthermore, in preferred embodiments the chief ray from a central one of the source elements propagates along or near the optical axis of the generalized optical system. Such systems also tend to produce smaller optical aberrations, and can optimize the field of view of the generalized optical system with respect to the light coming from the source array. Another criteria for optimizing the properties and positioning of the illuminator components is to optimize the light intensity throughput from each source element through the pinhole aperture and/or into a coupling fiber. This criteria may be the primary and/or only optimization criteria when a fiber is used to homogenize the spectral content of the beam across its transverse profile.

The spectral bands covered by the source array may vary depending on the end-use application. While many configurations are possible, one set of embodiments includes spectral channels at visible wavelengths of about 3 nm to 20 nm per band, with from 8 to 80 spectral bands overall. Where a given LED has a spectral width broader than that desired, the source element may include a band pass filter select a subset of the LED spectral profile.

For example, for 10 spectral bands spanning the range of 430 nm to 655 nm, band pass filters (e.g., interference filters) may be used to define a 25-nm interval for each band over that range. In general, choice of particular LEDs is dictated by the desired spectral coverage and brightness. It is possible to use bare LEDs of the type that emit vertically (normal to the chip surface), as well as to use packaged LEDs.

As is well known, the output flux from an LED varies with drive current, which is how the electronic controller selects the output of each channel. Typically a digital-to-analog (DAC) converter is used together with a current-output drive signal, with one such circuit for each LED. Unused channels may be turned off entirely. The electronic controller can further time-modulate the output of the source array. This can be useful to provide a blanking interval for use in reading out a digital camera or in time-resolved fluorescence measurements. In the latter case, modulation circuitry may be used alone or combined with multiplying DACs to achieve higher modulation speeds. In general, the circuitry used for driving the LEDs is well known.

Furthermore, in additional embodiments, the source element in the source array corresponding to a given wavelength band may include multiple LEDs to improve its brightness. Moreover, the source elements of the source array may include diode lasers, rather than, or in addition to LEDs. Furthermore, the source array may provide radiation derived from other sources such as non-diode lasers or lamps, which may couple light to the source array or be incorporated directly into the source array. In general, the source array can be formed by any discrete or continuous set of light sources that emit radiation at multiple wavelengths bands from corresponding positions of the array and whose intensity output can be varied through an electronic interface. For example, the intensity output may be varied directly by a drive signal to the source, or indirectly through the incorporation of a light shutter or variable attenuator with the source.

Figure 5A:
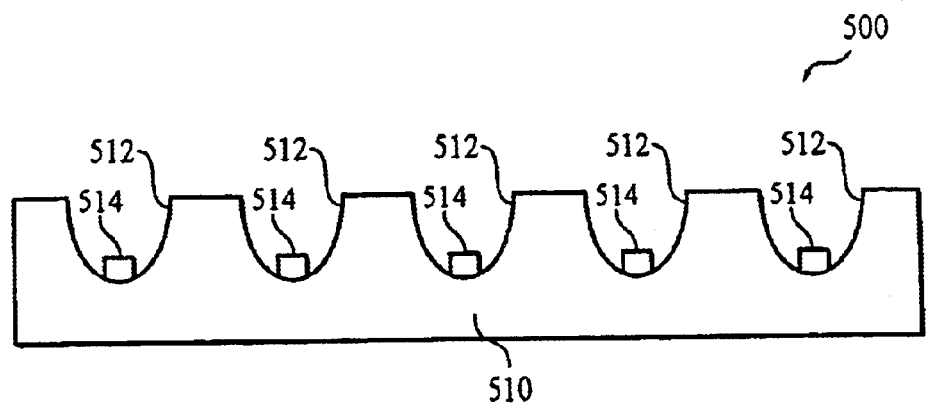
FIG. 5a is a schematic diagram of a source array 500 with reflective cups 512 to enhance forward emission.
Figure 5B:
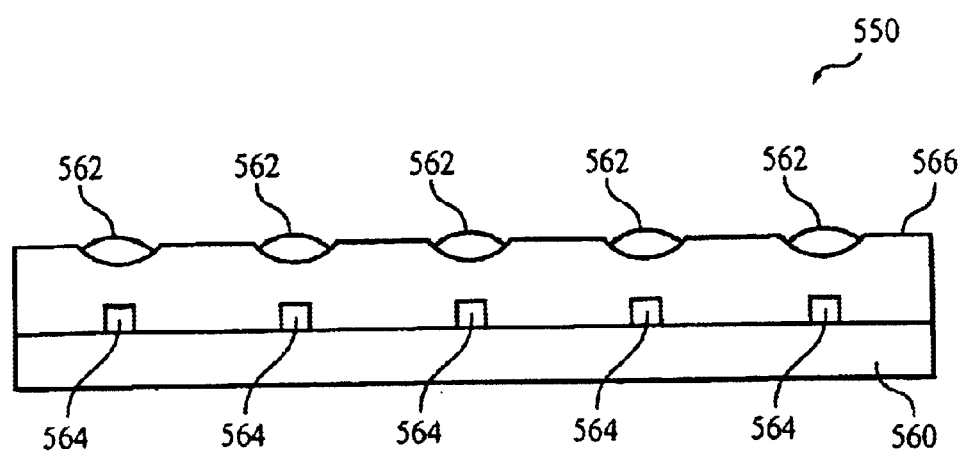
FIG. 5b is another schematic diagram of a source array 550 with a lenslet array 566.

The source array may further include any of the following modifications. Referring to FIG. 5a, to enhance the forward intensity of the different source elements 514 in a source array 500, the substrate 510 may support each element 514 in a corresponding reflective cup 512. Likewise, referring to FIG. 5b, a microlens 562 can be positioned adjacent each source element 564 in source array 550 to capture wide-angle light rays and direct them towards the other elements of the multispectral illuminator. Each microlens 562 can be part of a lenslet array 566 that is secured to a substrate 560 that supports source elements 564. In such embodiments, the reflective cups and/or microlenses are to be considered as part of the optical system that directs the radiation from each source element to the grating because they effect the image of the grating with respect to each source element.

The gratings in the multispectral illuminators described above may be any type of grating, e.g., a blazed grating, a holographic grating, an echelle gratings, etc. Furthermore, the grating may replaced by any other optical element that can provide the appropriate angular dispersion, such as a chromatic prism or a diffractive optical element.

Figure 6:
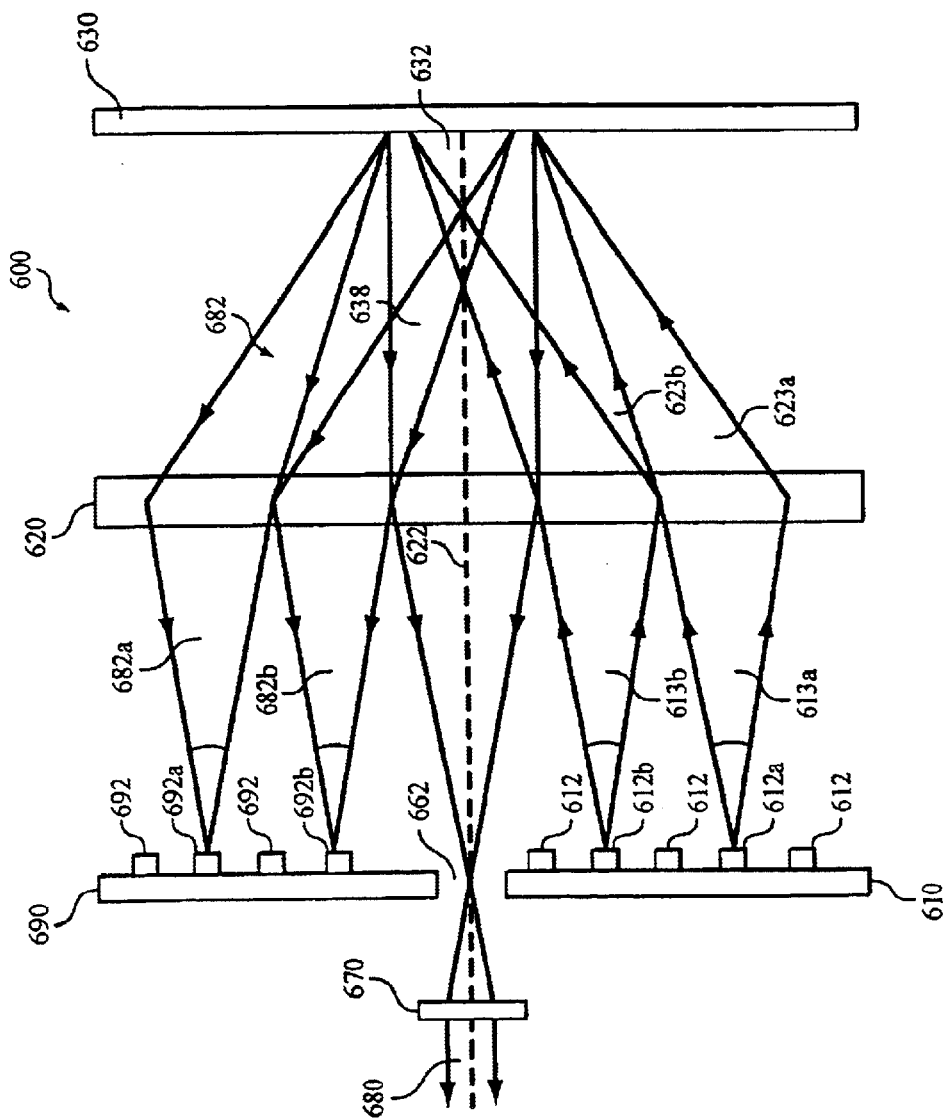
FIG. 6 is a schematic diagram of a multispectral illuminator 600 that involves monitoring beams 682.

We now describe embodiments of the multispectral illuminator system that include monitoring beams for monitoring the performance of the source array. Referring to FIG. 6, spectral lamp 600 includes a source array 610 having an array of source elements 612 providing EM radiation at corresponding wavelength bands. For example, source elements 612a and 612b provide radiation cones 613a and 613b at wavelengths $\lambda_A$ and $\lambda_B$, respectively. Multispectral illuminator 600 further includes a reflection grating 630 and a generalized optical system 620 that collimates the radiation cone from each point of each source element (to produce, for example, collimated radiation 623a and 623b corresponding to source elements 612a and 612b, respectively) and directs the collimated radiation from each point of each source to be coextensive on an active area 632 of reflection grating 630.

Reflection grating 630 causes a portion of the collimated radiation incident on it from each source element to diffract along a common direction substantially collinear with the optical axis 622 of optical system 620 to define output radiation 638. Output radiation 638 passes back through optical system 620, which focuses it to a pinhole 662 positioned coplanar with source array 610. The radiation that emerges from the pinhole can be collimated by a collimating lens 670 to produce an output beam 680, whose spectral content is substantially uniform across its transverse profile. As in the previous embodiments, a controller (not shown) independently controls the output of each source element to thereby select the spectral content of the output beam.

Reflection grating 630 reflects the remaining portion of the collimated radiation incident on it from each source element to produce monitoring beams 682. Optical system 620 then images monitoring beams 682 to a detector array 690 positioned coplanar with source array 610. Notably, reflection grating does not change the angular dispersion in the reflected radiation that produces monitoring beams 682. Thus, optical system 620 causes monitoring beams 682 to reconstruct an image of spatially separated source elements 612 on detector array 690. The detector array includes a detector element 692 for measuring the intensity of each monitoring beam, which in turn is indicative of the output from a corresponding one of the source elements. For example, detector elements 692a and 692b measure the intensities of monitoring beam 682a and 682b, respectively, which are derived from radiation cones 613a and 613b corresponding to the output from source elements 612a and 612b, respectively. Suitable detectors may include any of those described above for the detector in microscope 130.

The reflected beams from reflection grating 630 correspond to the zero order of diffraction, and most gratings have at least some efficiency in that order. Thus, one advantage of multispectral illuminator 600 is that the reflected light is measured to monitor the output of the source array, rather than wasted. More generally, in other embodiments, monitoring beams can be derived from a non-zero diffraction order that is different from the one used to produce the multispectral output radiation. For example, such embodiments include ones similar to that in FIG. 6 except that the reflection grating is not oriented perpendicular to the optical axis of the generalized optical system.

The intensity information measured by detector 690 is sent to the electronic controller to simultaneously provide an independent measure of the output of each source element. Such information may used by the electronic controller to calibrate the desired output for each element and/or to provide a feedback loop for producing a desired spectral profile in the output beam. Furthermore, where the electronic controller relies on some previously determined calibration curve for a given source element, the electronic controller can use the monitoring information to determine whether the calibration curve remains valid. For example, aging in an LED source may cause a calibration associating an output intensity with a drive current to change with time. Moreover, the monitoring information can immediately alert the electronic controller to a catastrophic breakdown in any of the source array elements.

Figure 7A:
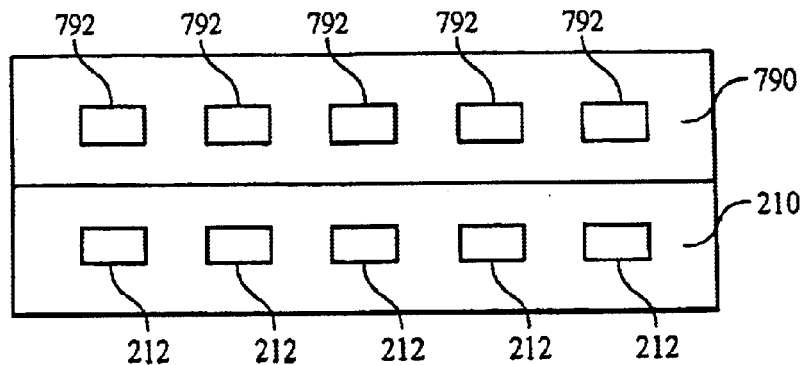
FIGS. 7a–7c are schematic diagrams of multispectral illuminator 200, which show how monitoring beams are used.

As mentioned above, multispectral illuminators 200 and 300 can also be configured to provide monitoring beams that independently measure the output of each source element. Details of such embodiments are now described. Referring to FIGS. 2a and 7a, multispectral illuminator 200 further includes a detector array 790 including multiple detector elements 792 positioned above (or below) source array 210 and source elements 212, where FIG. 7a is a plan view of the source and detector arrays perpendicular to the page of FIG.

2a. Each detector element 792 is configured to measure a monitoring beam derived the output of a correspond source element 212.

Figure 7B:
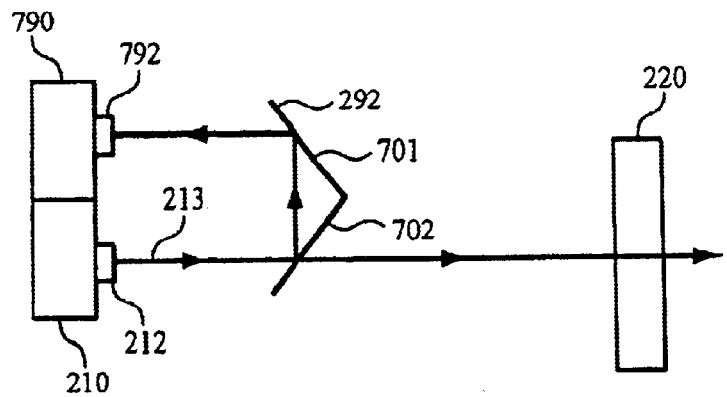

Referring now to FIG. 7b, an embodiment including monitoring optic 292 positioned between source array 210 and optical system 220 is shown, where FIG. 7b is a side view of multispectral illuminator 200 in a plane perpendicular to the page of FIG. 2a. Monitoring optic 292 is a roof prism extending parallel with the elements of source array 210. The lower part 702 of the roof prism is highly transparent (e.g., it may have include an anti-reflection coating) and reflects only a small part of each radiation cone 213 from source array 210 as a corresponding monitoring beam 713. The transmitted parts of radiation cones 213 propagate towards optical system 220 to ultimately form the output beam. The monitoring beams, on the other hand, are reflected by the upper part 704 of the roof prism to direct them to the corresponding elements of detector array 790, which measure their respective intensities.

Figure 7C:
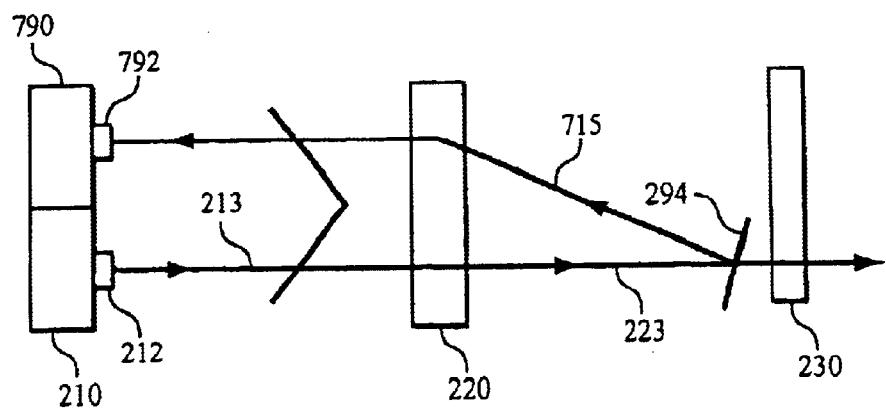

Referring now to FIG. 7c, an embodiment including monitoring optic 294 positioned between optical system 220 and dispersive element 230 is shown, where FIG. 7c is a side view of multispectral illuminator 200 in a plane perpendicular to the page of FIG. 2a. Monitoring optic 294 is a pick-off mirror extending parallel with the elements of source array 210 and positioned immediately adjacent grating 230. The pick-off mirror is highly transparent (e.g., it may have include an anti-reflection coating) and reflects only a small part of the collimated radiation 223 from each source element as a corresponding monitoring beam 715. The transmitted parts of the collimated radiation 213 are diffracted by grating 230 to ultimately form the output beam. The monitoring beams, on the other hand, are reflected by the pick-off mirror back towards optical system 220. The pick-off mirror is tilted slightly to deflect the monitoring beams upwards. Because of the deflection, optical system 220 directs the monitoring beams to detector array 790 and constructs a vertically displaced image of the source array, with the image of each source element overlapping with its corresponding detector element.

The arrangements shown in FIGS. 7a–7c can be similarly incorporated into the folded multispectral illuminator design (multispectral illuminator 300) shown in FIG. 3a. Furthermore, in additional embodiments, the respective monitoring optic can be any optic or optics that provides the same functionality as that shown in FIGS. 7b and 7c. For example, in the embodiment of FIG. 7b, the roof prism can be replace with two separate elements, a lower beam-splitter and an upper mirror oriented similarly to the lower and upper parts, respectively, of the roof prism. In another example, in the embodiment of FIG. 7c, the tilted pick-off mirror can be replaced with a wedge having a tilted face.

Furthermore, in an additional embodiment, the monitoring optic can be a beam splitter positioned between the source array and the optical system at an angle to the source array to derive a set of monitoring beams from the radiations cones emitted by the source array and direct them to a separately positioned detector array.

Figure 8A:
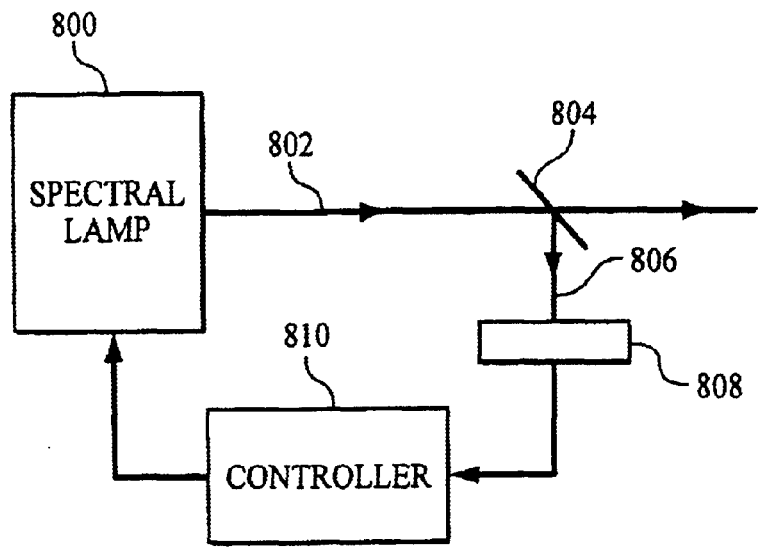
FIGS. 8a–8b are schematic diagrams of a multispectral illuminator 800 and components for monitoring the output of the lamp.
Figure 8B:
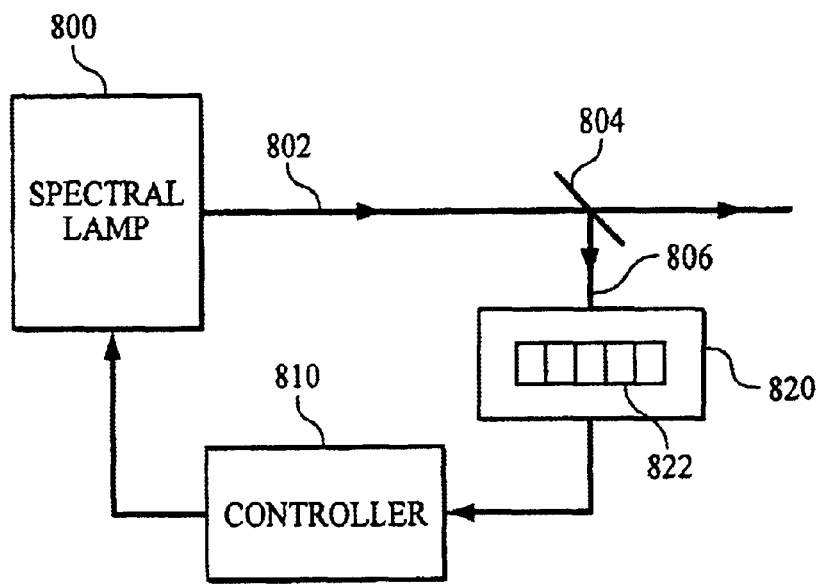

It is also possible to monitor the performance of the elements of the source array by deriving a monitor beam from the multi-spectral output radiation or output beam produced by the multispectral illuminator. Two such embodiments are shown in FIGS. 8a and 8b. Referring to FIG. 8a, multispectral illuminator 800 produces multispectral output beam 802, and a beam splitter 804 deflects a small portion of the output beam to produce monitor beam 806, whose intensity is measured by detector 808. The detector sends the intensity information to controller 810, which is coupled to multispectral illuminator 800 to control the spectral content of output beam 802. To monitor the performance of a particular source element, controller 810 adjusts the spectral content of the output beam 802 to nominally include only the wavelength band corresponding to the source element in question. Although this embodiment is relatively simple, it has the drawback that the performance of multiple source elements cannot be monitored simultaneously. Referring to the FIG. 8b, the detector 808 is replaced by a spectrometer 820 that spatially separates the spectral components of monitor beam 806 and a multi-element detector 822 that measures the intensities of the spatially separated spectral components of the monitor beam. As a result, multi-element detector 822 independently and simultaneously monitors the output of each of the source elements, and sends this information to electronic controller 810.

Figure 9A:
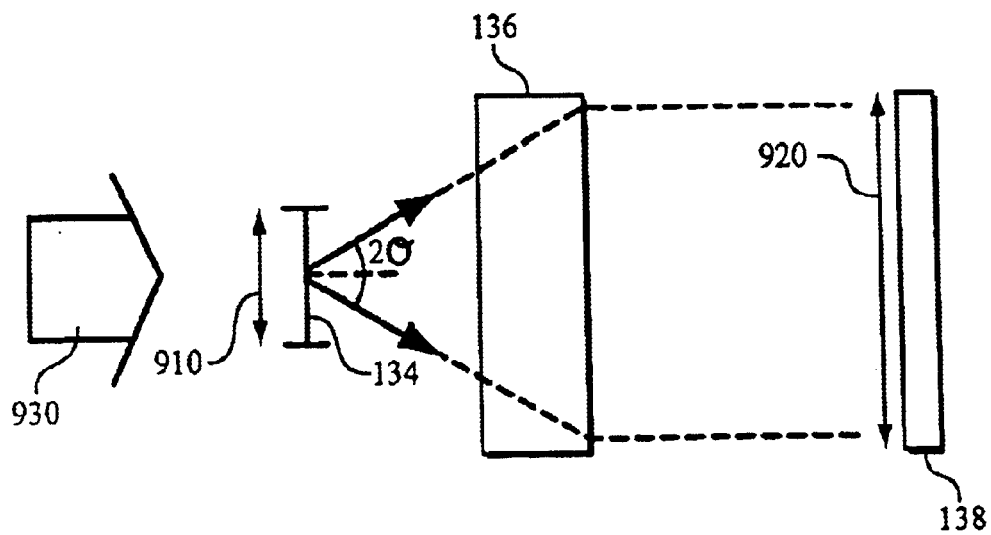
FIG. 9a is schematic diagram showing how microscope 130 collects the light from sample 134 to produce an image 920 on detector 138 in response to illumination pattern 930.

Referring again to FIG. 1, we now discuss beam modification optics 120. As mentioned above, the beam modification optics are selected to improve the light efficiency, field of view, and resolution of microscope 130. Generally, detection optics 136 in the microscope reconstruct an image of sample 134 on imaging detector 138. Referring to FIG. 9a, the magnification of detection optics 136 and the size 920 of imaging detector 138 are designed to accommodate a given sample area 910. The resolution of the sample image on imaging detector 138 will depend on the numerical aperture of detection optics 136, which can be expressed as the half-angle $\phi$ of the cone of rays emerging from each point of sample area 910 that is collected by detection optics 136. For example, rays emerging from the sample area outside of numerical aperture cone 912 are lost and do not reach the imaging detector. Generally, detection optics 136 are designed to maximize the numerical aperture $\phi$, and thereby maximize resolution, for a given sample area, subject to any practical limitations on the size 920 of the imaging detector.

Notably, portions of the illumination pattern 930 (derived from the multispectral illuminator) that are incident on sample 134 outside the sample area do not reach imaging detector 138 and are ultimately wasted. Likewise, portions of the illumination pattern 930 that are incident on sample 134 outside the corresponding numerical aperture cone do not reach imaging detector 138 and are ultimately wasted. Conversely, when the divergence of illumination pattern 930 does not fill the numerical aperture cone at each point of the sample area, the full resolution of detection optics 136 is not obtained. Accordingly, the beam modifications optics are used insure that the illumination pattern fills the numerical aperture cone at every point of the sample area, but does not otherwise waste light (i.e., the illumination pattern does not extend to far beyond the sample area and does not diverge to far beyond the numerical aperture cone defined by the detection optics).

Figure 9C:
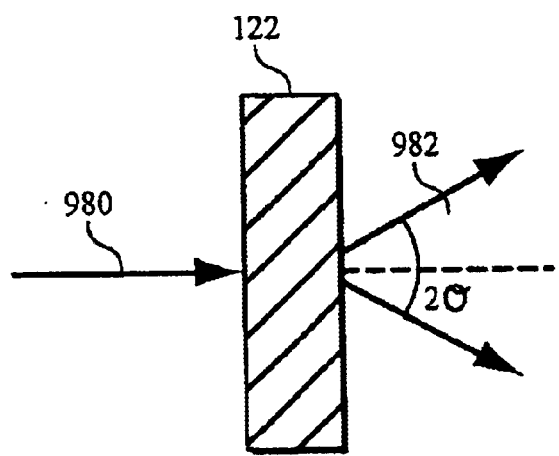
FIG. 9c is a schematic drawing of a diffuser 122 and its affect on an input ray 980.
Figure 9B:
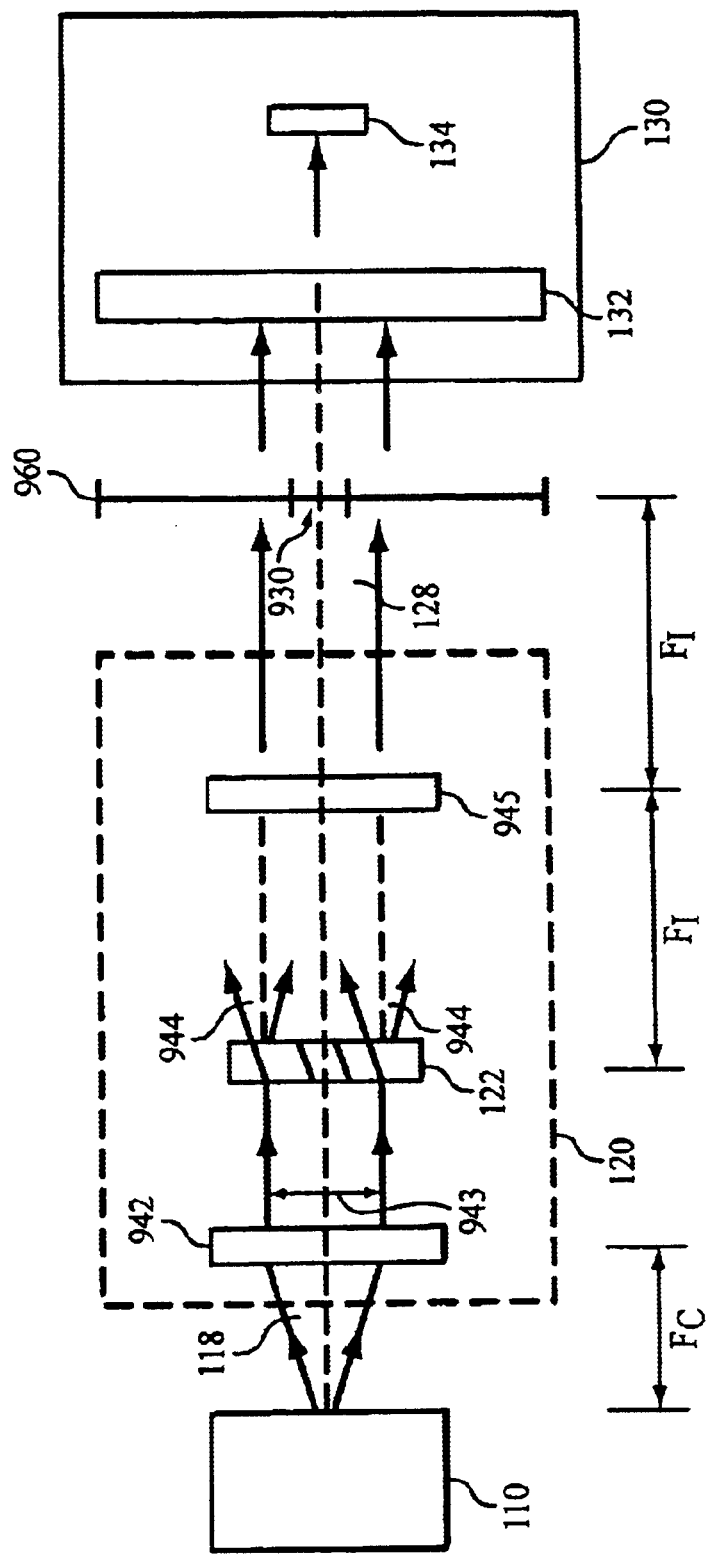
FIG. 9b is a schematic diagram of beam modification optics 120 used to modify the output beam 118 from multispectral illuminator 110 to produce image 950 in the input image plane 960 of microscope 130.

Referring now to FIGS. 1 and 9b, multispectral illuminator 110 produces output beam 118, which, for example, corresponds to the light emerging from pinholes 262 or 362 from the embodiments of FIG. 2 or 3, respectively, or from a fiber. Beam modification optics 120 are positioned to receive output beam 118 and produce modified output beam 128, which forms an image 950 in an input image plane 960 of microscope 130. Source optics 132 in microscope 130 reconstruct image 950 on sample 134 to define the illumination pattern. According to the principles described in the preceding paragraph, beam modification optics 120 modifies output beam 118 so that image 950, when reconstructed on sample 134 by the microscope, fills the numerical aperture cone at every point of the sample area, but does not otherwise waste light. To provide such modification, beam modification optics independently control the spot size and divergence cone of output beam 118.

To modify the divergence cone of the output beam, beam modification optics 120 include a diffuser 122, such as a holographic diffuser. Referring to FIG. 9c, an input ray 980 to diffuser 122 fills a divergence cone 982 upon exiting the diffuser. The size of the divergence cone (quantified by half-angle φ) is a property of the diffuser and the diffuser can be selected to provide a desired divergence. Suitable holographic diffuser are well known in the art and are available commercially from, for example, Physical Optics Corporation (CA) and are commercially available with full-width, half-maximum scattering angles of 10°, 15°, 20°, 25°, 30°, 40°, 60°, and 80°. The diffuser may also be opal diffusing glass, e.g., one surface is "opal" coated to achieve a near Lambertian source—the large diffusion causes a large amount of scattering loss. For example, the opal layer thickness may be approximately 0.45 mm thick. Opal diffusing glass is commercially available from Edmund Industrial Optics (NJ). The diffuser may also be ground glass. For example, it could be glass ground on one side with single or orthogonal double passes of 120 or 220 grit sandblast. Ground glass diffusers are also commercially available from Edmund Industrial Optics (NJ).

The beam modifications optics can further include one or more lenses (or curved reflective optics) for modifying (e.g., magnifying or demagnifying) the spot size of output beam 118.

In the particular embodiment shown in FIG. 9b, beam modification optics include a collimating lens 942, diffuser 122, and an injection lens 945. Output beam 118 diverges as it exits multispectral illuminator 110, and collimating lens 942 is positioned to collimate the output beam. Accordingly, the focal length "$F_C$" of collimating lens 942 defines a spot size 943 for the output beam and is selected to provide selected spot size. The collimated output beam is then incident on diffuser 122, which imparts a selected divergence cone 944 across the collimated output beam. Injection lens 945 has focal length "$F_1$" and is positioned such that diffuser 122 and input image plane 960 lie in its back and front focal planes, respectively. The injection lens then produces the Fourier transform image of the light emerging from diffuser 122 at the input image plane to define image 950. As a result of the Fourier transform by the injection lens, the focal length "$F_C$" of collimating lens 942 controls the divergence cone across image 950 (and hence the divergence cone across the illumination pattern on the sample), and the divergence cone imparted by diffuser 122 controls the spot size of image 950 (and hence the spot size of the illumination pattern on the sample).

In additional embodiments, the beam modification optics may not include the injection lens, and so the divergence cone imparted by the diffuser may correspond directly to the divergence cone across the image in the input image plane of the microscope. Similarly, in such embodiments the spot size formed by the collimating lens may correspond directly to the spot size of the image in the input image plane. In either case, the diffuser and collimating lens provide independent control over the spot size and divergence cone of the illumination pattern on the sample. In other words, the diffuser controls one of the spot size and the divergence cone of the illumination pattern, but not the other, and vice versa for the collimating lens. Thus, selecting a desired spot size and/or divergence cone of the illumination pattern corresponds directly to selecting the divergence cone for the diffuser and/or the focal length of the collimating lens.

Moreover, to accommodate different sample areas and/or changes in the magnification of the microscope, or even the use of a different microscope (or macroscope), the beam modification optics may include multiple diffuser elements each producing a different divergence cone. Each diffuser may be selectably positioned to receive the light from collimating lens 942 and thereby impart a selected divergence cone to the incident light. Similarly, the beam modification optics may include multiple lenses having different focal lengths, each of which may be selectively positioned to collimate output beam 118 and produce a selected spot size 943. By controlling both spot size 943 and divergence cone 944, the beam modification optics can selectively control the spot size and divergence cone of its output light for any end-use application. Furthermore, the selection is relatively simple because the collimating lens and diffuser provide independent control over spot size 943 and divergence cone 944, respectively. Thus, the beam modification optics increase the versatility of the multispectral illuminator and enable efficient light harvesting for multiple end-use applications.

The multiple diffusers may include separate elements, wherein the selected element for a given application is positioned robotically or by hand (in a mount, for example) to intercept that collimated light from lens 942. Alternatively, the multiple diffusers may be secured together. For example, they may be secured to a common substrate that defines a slider that can translate to position the selected diffuser into the light beam path. In another example, the diffuser elements may be secured to a wheel that can be rotated to position the selected diffuser into the light beam path. Likewise, the multiple collimating lenses may also be separate elements that are positioned by hand or robot, or they may be secured together to provide more convenient selection of one focal length over another. When selecting a particular lens (or lens element), however, the axial position of the selected lens needs to be adjusted to properly collimate beam 118 according to its focal length. To facilitate such positioning, a mount for the collimating lens can be secured to a translation stage that positions the mount to corresponding axial positions corresponding to the different focal lengths of the multiple lenses.

Other configurations for the beam modification optics are also possible. For example, the positions of the elements in FIGS. 9a–9b may be permuted and/or there may be additional elements. In general, the beam modification optics include one or more diffusers and, if desired, one or more additional optics (e.g., lenses and/or curved reflective optics) to produce a desired divergence cone and spot size for the input light to the microscope. Preferably, the desired divergence cone and spot size are selected so that the illumination pattern on the sample fills the numerical aperture cone at every point of the sample area, but does not otherwise waste light. Furthermore, the beam modification optics may include multiple diffusers and/or lenses that are selectively positioned into the beam path to produce a selectable spot size and divergence cone for the modified output light and thereby accommodate a corresponding array of field of views and numerical apertures for a downstream application. For example, the system may incorporate such elements as linear or rotary sliders that engage these elements either singly or in combination. Furthermore, as a described in the embodiment above, the elements can be arranged to provide independent control over the spot size and divergence cone.

A number of embodiments of the invention have been described. Nevertheless, it will be understood that various modifications may be made without departing from the spirit and scope of the invention.

What is claimed is:

1. A multispectral illuminator for providing EM radiation with a selectable frequency content, the multispectral illuminator comprising:

a dispersive element which during operation provides an angular dispersion for incident EM radiation;

a light source array comprising an array of light sources providing EM radiation at different wavelengths; and an optical system having an optical power, the optical system positioned relative to the source array and the dispersive element to image the dispersive element at infinity with respect to the light source array for at least one of the different wavelengths in a paraxial approximation, wherein the position of each light source along the array and the angular dispersion of the dispersive element are selected to cause at least a portion of the EM radiation from the source array incident on the dispersive element through the optical system to propagate along a common direction.

2. The multispectral illuminator of claim 1, wherein during operation the optical system collimates the EM radiation emerging from each light source within a preset cone angle and directs the collimated radiation from each light source to be coextensive on the diffractive element.

3. The multispectral illuminator of claim 1, wherein the optical system defines a focal length for at least one of the different wavelengths and wherein the light source array and the dispersive element are each spaced from the optical system by a distance substantially equal to the focal length.

4. The multispectral illuminator of claim 1, wherein the spatial extent of the dispersive element defines an aperture stop for the optical system.

5. The multispectral illuminator of claim 4, wherein the dispersive element includes an iris for varying the spatial extent of the dispersive element.

6. The multispectral illuminator of claim 1, wherein the optical system and the dispersive element cause the EM radiation propagating along the common direction to have a spatial distribution that is substantially wavelength independent.

7. The multispectral illuminator of claim 1, wherein the common direction is substantially collinear with a chief ray from a central one of the light sources.

8. The multispectral illuminator of claim 1, wherein the dispersive element is a reflective dispersive element.

9. The multispectral illuminator of claim 8, wherein the reflective dispersive element is a reflective grating.

10. The multispectral illuminator of claim 8, wherein the reflective dispersive element directs the radiation back to the optical system along the common direction and wherein the optical system focuses the radiation received from the reflective dispersive element to a spot in an image field.

11. The multispectral illuminator of claim 10, wherein the image field is substantially coplanar with a plane defined by the source array.

12. The multispectral illuminator of claim 10, wherein the common direction is substantially perpendicular to a plane defined by the source array.

13. The multispectral illuminator of claim 10, wherein the source array comprises a substrate supporting the light sources and wherein the spot in the image field coincides with an aperture in the substrate.

14. The multispectral illuminator of claim 13, wherein the light sources extend along an axis, and wherein the aperture lies along the light source axis.

15. The multispectral illuminator of claim 13, wherein the light sources extend along an axis, and wherein the aperture lies above or below the light source axis.

16. The multispectral illuminator of claim 10, wherein the optical system forms a telecentric imaging system.

17. The multispectral illuminator of claim 13, further comprising an optical fiber positioned to receive the focused radiation from the aperture in the substrtate.

18. The multispectral illuminator of claim 1, wherein the dispersive element is a transmissive dispersive element.

19. The multispectral illuminator of claim 18, wherein the transmissive dispersive element is a transmission grating.

20. The multispectral illuminator of claim 18 further comprising a second optical system position to receive the radiation from the transmissive dispersive element propagating along the common direction and focus it to a spot in an image field.

21. The multispectral illuminator of claim 20, wherein the common direction is substantially perpendicular to a plane defined by the source array.

22. The multispectral illuminator of claim 20, wherein the optical systems form a telecentric imaging system.

23. The multispectral illuminator of claim 20, wherein the second optical system defines a focal length, and wherein the transmissive dispersive element and the image field are each spaced from the second optical system by a distance substantially equal to the focal length of the second optical system.

24. The multispectral illuminator of claim 20, further comprising an optical fiber positioned to receive the focused radiation from the spot in the image field.

25. The multispectral illuminator of claim 1, wherein the optical system comprises a singlet lens.

26. The multispectral illuminator of claim 1, wherein the optical system comprises a composite lens system.

27. The multispectral illuminator of claim 1, wherein the optical system comprises at least one curved reflective surface.

28. The multispectral illuminator of claim 1, further comprising an electronic controller coupled to the array of light source for selectively adjusting the EM radiation provided by each light source.

29. The multispectral illuminator of claim 1, wherein the EM radiation provided by the array of light sources span wavelengths within the range of 400 nm to 1000 nm.

30. The multispectral illuminator of claim 1, wherein the source array comprises a substrate supporting the light sources, and wherein each light source comprises at least one light emitting diode (LED) mounted on the substrate.

31. The multispectral illuminator of claim 30, wherein each light source comprises multiple light emitting diodes (LED) mounted on the substrate.

32. The multispectral illuminator of claim 1, wherein the source array comprises a substrate supporting the light sources, and wherein the substrate further supports a reflective cup surrounding each light source to enhance light emission from the light sources in a forward direction.

33. The multispectral illuminator of claim 1, wherein the light source array further comprises a lenslet array aligned with the array of light sources.

34. A multispectral illuminator for providing EM radiation with a selectable frequency content, the multispectral illuminator comprising:

a dispersive element which during operation provides an angular dispersion for incident EM radiation;

a light source array comprising an array of light sources providing EM radiation at different wavelengths; and an optical system having an optical power, wherein during operation the optical system collimates the EM radiation emerging from each light source within a preset cone angle and directs the collimated radiation from each light source to be coextensive on the diffractive element, and wherein the position of each light source along the array and the angular dispersion of the dispersive element are selected to cause at least a portion of the EM radiation from the source array incident on the dispersive element through the optical system to propagate along a common direction.

35. A multispectral illuminator for providing EM radiation with a selectable frequency content, the multispectral illuminator comprising:

a dispersive element which during operation provides an angular dispersion for incident EM radiation;

a light source array comprising an array of light sources providing EM radiation at different wavelengths; and an optical system having an optical power, wherein the optical system defines a focal length for at least one of the different wavelengths and wherein the light source array and the dispersive element are each spaced from the optical system by a distance substantially equal to the focal length, and wherein the position of each light source along the array and the angular dispersion of the dispersive element are selected to cause at least a portion of the EM radiation from the source array incident on the dispersive element through the optical system to propagate along a common direction.

36. The multispectral illuminator of claim 1, wherein the source array supports at least two of the light sources at different axial positions relative to the optical system to reduce at least one of field curvature and axial chromatic aberration in the collimated EM radiation incident on the dispersive element.

37. The multispectral illuminator of claim 36, wherein the substrate has a curved surface supporting the light sources.

38. The multispectral illuminator of claim 1, wherein the source array supports at least two of the light sources at lateral positions along the array that reduce at least one of distortion and lateral chromatic aberration in the collimated EM radiation incident on the dispersive element.

39. The multispectral illuminator of claim 38, wherein the substrate supports the light sources at lateral positions along the array that vary nonlinearly with the central frequency of the EM radiation provided by each light source.

40. A multispectral illuminator for providing EM radiation with a selectable frequency content, the multispectral illuminator comprising:

a dispersive element which during operation provides an angular dispersion for incident EM radiation;

a light source array comprising a substrate supporting an array of light sources providing EM radiation at different wavelengths; and an optical system having an optical power, the optical system positioned to direct light from the light source array to the dispersive element, wherein the position of each light source along the array and the angular dispersion of the dispersive element are selected to cause EM radiation from the source array incident on the diffractive element through the optical system to propagate along a common direction, and wherein the substrate supports at least two of the light sources at different axial positions relative to the optical system to reduce at least one of field curvature and axial chromatic aberration in the collimated EM radiation incident on the dispersive element.

41. The multispectral illuminator of claim 1, further comprising beam modification optics positioned to receive light derived the EM radiation propagating along the common direction and produce an illumination pattern having a desired spot size and a desired divergence cone across the spot size.

42. The multispectral illuminator of claim 41, wherein the beam modification optics comprise a diffuser for modifying the divergence of an incident beam.

43. The multispectral illuminator of claim 42, wherein the beam modification optics comprise multiple diffusers each providing a different scattering cone and wherein each of the multiple diffusers can be selectably positioned to intercept the light derived from the EM radiation propagating along the common direction.

44. The multispectral illuminator of claim 42, wherein the beam modification optics further comprise at least one lens.

45. The multispectral illuminator of claim 44, wherein the beam modification optics further comprise multiple lenses having different focal lengths and wherein each of the multiple lenses can be selectably positioned to intercept the light derived from the EM radiation propagating along the common direction.

46. The multispectral illuminator of claim 42, wherein the diffuser is a holographic diffuser.

47. A spectral imaging system comprising:

the multispectral illuminator of claim 1;

beam delivery optics positioned to form an illumination pattern on a sample based on the EM radiation produced by the multispectral illuminator;

an detection optics positioned to receive light from the sample in response to the illumination pattern and form an image of the sample in a focal plane; and an imaging detector located in the focal plane for detecting and spatially resolving the image of the sample.

48. The spectral imaging system of claim 47, wherein the detection optics is a lens.

49. The spectral imaging system of claim 47, wherein the beam delivery optics comprise a diffuser for controlling the divergence of an incident beam.

50. The spectral imaging system of claim 49, wherein the beam delivery optics comprise multiple diffusers each providing a different scattering cone and wherein each of the multiple diffusers can be selectably positioned to intercept EM radiation used to form the illumination pattern.

51. The spectral imaging system of claim 50, wherein the beam delivery optics further comprise at least one lens.

52. The spectral imaging system of claim 51, wherein the beam delivery optics further comprise multiple lenses having different focal lengths and wherein each of the multiple lenses can be selectably positioned to intercept the light derived from the EM radiation used to form the illumination pattern.

53. The spectral imaging system of claim 49, wherein the diffuser is a holographic diffuser.

54. The spectral imaging system of claim 47, wherein the detection optics collect light within a numerical aperture, and wherein the beam delivery optics cause the EM radiation in the illumination pattern incident on the sample to fill the numerical aperture of the detection optics.

55. The spectral imaging system of claim 54, wherein the detection optics collect light from the sample over a sample area for light rays emerging from the sample area within the numerical aperture, and wherein the beam delivery optics cause the illumination pattern to fill the sample area and the numerical aperture.

56. A spectral imaging system comprising:
   a multispectral illuminator producing EM radiation, the illuminator comprising an array of sources at different wavelengths;
   beam modification optics positioned to form an illumination pattern on a sample based on the EM radiation produced by the multispectral illuminator, the illumination pattern having a desired spot size and a desired divergence cone across the spot size, the beam modification optics comprising a diffuser for controlling at least one of the spot size and divergence cone of the illumination pattern;
   detection optics positioned to receive light from the sample in response to the illumination pattern and form an image of the sample in a focal plane; and
   an imaging detector located in the focal plane for detecting and spatially resolving the image of the sample.

57. The spectral imaging system of claim 56, wherein the EM radiation produced by the multispectral illuminator has a substantially spectrally uniform spatial profile.

58. The spectral imaging system of claim 56, wherein the detection optics is a lens.

59. The spectral imaging system of claim 56, wherein the diffuser is a holographic diffuser.

60. The spectral imaging system of claim 56, wherein the beam modification optics comprise multiple diffusers each providing a different scattering cone and wherein each of the multiple diffusers can be selectably positioned to intercept EM radiation used to form the illumination pattern.

61. The spectral imaging system of claim 56, wherein the beam modification optics further comprise at least one lens.

62. The multispectral illuminator of claim 61, wherein the beam modification optics further comprise multiple lenses having different focal lengths and wherein each of the multiple lenses can be selectably positioned to intercept the light derived from the EM radiation used to form the illumination pattern.

63. The spectral imaging system of claim 56, wherein the detection optics collect light within a numerical aperture, and wherein the beam delivery optics cause the EM radiation in the illumination pattern incident on the sample to fill the numerical aperture of the detection optics.

64. The spectral imaging system of claim 63, wherein the detection optics collect light from the sample over a sample area for light rays emerging from the sample area within the numerical aperture, and wherein the beam delivery optics cause the illumination pattern to fill the sample area and the numerical aperture.

65. The multispectral illuminator of claim 1, further comprising a detector positioned to receive a monitoring beam derived from a portion the EM radiation propagating along the common direction.

66. The multispectral illuminator of claim 1, further comprising a multi-channel detector positioned to receive an array of monitoring beams derived from the EM radiation provided by the source array, wherein each monitoring beam corresponds to one of the light sources.

67. The multispectral illuminator of claim 66, further comprising a monitoring beam optic positioned between the source array and the optical system for producing the monitoring beams from corresponding portions of the EM radiation provided by the light sources.

68. The multispectral illuminator of claim 67, wherein the monitoring beam optic comprises a partially transparent roof mirror extending parallel to the array of light sources.

69. The multispectral illuminator of claim 66, wherein the dispersive element causes the first portion of the incident EM radiation from the light sources to propagate along the common direction, and causes a second portion of the incident EM radiation to form the monitoring beams.

70. The multispectral illuminator of claim 69, wherein the dispersive element reflects the second portion to form the monitoring beams.

71. The multispectral illuminator of claim 69, wherein the dispersive element transmits the second portion to form the monitoring beams.

72. The multispectral illuminator of claim 69, wherein the dispersive element diffracts the first portion to cause it to propagate along the common direction, and diffracts the second portion along an order different from that of the first portion to form the monitoring beams.

73. The multispectral illuminator of claim 69, wherein the monitoring beams propagate through the optical system prior to being received by the multi-channel detector.

74. The multispectral illuminator of claim 66, further comprising a monitoring beam optic positioned between the optical system and the dispersive element to produce the monitoring beams from a portion of the EM radiation being imaged by the optical system.

75. The multispectral illuminator of claim 74, wherein the monitoring beams propagate through the optical system prior to being received by the multi-channel detector.

76. The multispectral illuminator of claim 75, wherein the monitoring beam optic is a wedge positioned immediately adjacent the dispersive element.

77. The multispectral illuminator of claim 76, wherein the multi-channel detector is positioned above or below the array of sources and the optical system directs the monitoring beams from the monitoring beam optic to form an image of the source array on the multi-channel detector.

78. The multispectral illuminator of claim 77, wherein a substrate in the source array supports the multi-channel detector.

79. The multispectral illuminator of claim 66, wherein the multi-channel detector is positioned above or below the array of sources.

80. The multispectral illuminator of claim 79, wherein a substrate in the source array supports the multi-channel detector.

81. A multispectral illuminator for providing EM radiation with a selectable frequency content, the multispectral illuminator comprising:
   a dispersive element which during operation provides an angular dispersion for incident EM radiation;
   a light source array comprising an array of light sources providing EM radiation at different wavelengths;
   an optical system having an optical power, the optical system positioned to direct light from the light source array to the dispersive element, and
   a multi-channel detector positioned to receive an array of monitoring beams derived from the EM radiation provided by the source array, each monitoring beam corresponding to one of the light sources,
   wherein the position of each light source along the array and the angular dispersion of the dispersive element are selected to cause EM radiation from the source array incident on the diffractive element through the optical system to propagate along a common direction.

82. A spectral imaging system comprising:
   the multispectral illuminator of claim 81;
   beam delivery optics positioned to form an illumination pattern on a sample based on the EM radiation produced by the multispectral illuminator;

detection optics position to receive light from the sample in response to the illumination pattern and form an image of the sample in a focal plane; and an imaging detector located in the focal plane for detecting and spatially resolving the image of the sample.

83. The multispectral illuminator of claim 81, further comprising a monitoring beam optic positioned between the source array and the optical system for producing the monitoring beams from corresponding portions of the EM radiation provided by the light sources.

84. The multispectral illuminator of claim 81, wherein the dispersive element causes the first portion of the incident EM radiation from the light sources to propagate along the common direction, and causes a second portion of the incident EM radiation to form the monitoring beams.

85. The multispectral illuminator of claim 84, wherein the dispersive element reflects the second portion to form the monitoring beams.

86. The multispectral illuminator of claim 84, wherein the dispersive element transmits the second portion to form the monitoring beams.

87. The multispectral illuminator of claim 84, wherein the dispersive element diffracts the first portion to cause it to propagate along the common direction, and diffracts the second portion along an order different from that of the first portion to form the monitoring beams.

88. The multispectral illuminator of claim 84, wherein the monitoring beams propagate through the optical system prior to being received by the multi-channel detector.

89. The multispectral illuminator of claim 81, further comprising a monitoring beam optic positioned between the optical system and the dispersive element to produce the monitoring beams from a portion of the EM radiation being directed by the optical system.

90. The multispectral illuminator of claim 89, wherein the monitoring beams propagate through the optical system prior to being received by the multi-channel detector.

91. The multispectral illuminator of claim 90, wherein the monitoring beam optic is a wedge positioned immediately adjacent the dispersive element.

92. The multispectral illuminator of claim 91, wherein the multi-channel detector is positioned above or below the array of sources and the optical system directs the monitoring beams from the monitoring beam optic to form an image of the source array on the multi-channel detector.

93. The multispectral illuminator of claim 92, wherein a substrate in the source array supports the multi-channel detector.

94. The multispectral illuminator of claim 81, wherein the multi-channel detector is positioned above or below the array of sources.

95. The multispectral illuminator of claim 94, wherein a substrate in the source array supports the multi-channel detector.

* * * * *

UNITED STATES PATENT AND TRADEMARK OFFICE
CERTIFICATE OF CORRECTION

PATENT NO. : 6,825,930 B2
DATED : November 30, 2004
INVENTOR(S) : Dan Orband et al.

It is certified that error appears in the above-identified patent and that said Letters Patent is hereby corrected as shown below:

Title page,
Item [56], References Cited, U.S. PATENT DOCUMENTS, insert the following references:

| | | | |
|---|---|---|---|
| 4,379,233 | 05/1983 | Rosenthal | 250/553 |
| 4,800,279 | 01/1989 | Hieftji et al. | 250/339.09 |
| 5,042,893 | 08/1991 | Ong | 385/49 |
| 5,137,364 | 08/1992 | McCarthy | 356/402 |
| 5,424,545 | 01/1995 | Block et al. | 250/343 |
| 5,433,197 | 07/1995 | Stark | 600/319 |
| 5,539,517 | 07/1996 | Cabib et al. | 356/456 |
| 5,567,937 | 10/1996 | Pinkus | 250/252.1 |
| 5,608,213 | 03/1997 | Pinkus et al. | 250/252.1 |
| 5,719,024 | 02/1998 | Cabib et al. | 435/6 |
| 5,760,407 | 06/1998 | Margosiak et al. | 250/461.2 |
| 5,838,451 | 11/1998 | McCarthy | 356/406 |
| 6,142,629 | 11/2000 | Adel et al. | 351/206 |
| 6,373,568 | 04/16/02 | Miller et al. | 356/326 |

OTHER PUBLICATIONS, insert the following references:

W.C. Sweatt et al., "ISIS; An Information-Efficient Spectral Imaging System," Imaging Spectrometry IV," Proc. SPIE, Vol.3438, pp. 98-106, San Diego, 1998.

B.R. Stallard, Contstruction of Filter Vectors for the Information-Efficient Spectral Imaging Sensor," Imaging Spectroscopy IV, Proc. SPIE, Vol 3438, pp. 172-182, San Diego, 1998.

L.O. Jimenez et al., "High Dimensional Feature Reduction via Projection Pursuit," TR-ECE 96-5, School of Electrical Engineering, Purdue University, West Lafayette, IN 47907-1285, April, 1995.

Hyvarien et al., "Novel Spectroscopic Techniques for Biomedical Applications," Optoelectronics Laboratory, Finland, SPIE Vol. 2084, pp. 224-230.

J. Malinen et al., "Thirty-two Channel LED Array Spectrometer Module with Compact Optomechanical Construction," Technical Research Centre of Finland, Electronics Laboratory, Finland, SPIE Vol. 1533 Optomechanics and Dimensional Stability (1991), pp. 122-128.

Gentry et al., "Biomedical Applications of the Information-Efficient Spectral Imaging Sensor (ISIS), Gentry, SPIE Vol. 3603, pp. 129-142.

Shnitser et al., "Spectrally Adaptive Light Filtering," Physical Optics Corporation, Torrance, CA, SPIE Vol. 3140, pp. 117-127.

UNITED STATES PATENT AND TRADEMARK OFFICE
CERTIFICATE OF CORRECTION

PATENT NO.   : 6,825,930 B2
DATED        : November 30, 2004
INVENTOR(S)  : Dan Orband et al.

It is certified that error appears in the above-identified patent and that said Letters Patent is hereby corrected as shown below:

Title page (cont'd),
   Jimenez et al., "Supervised Classification in High Dimensional Space: Geometrical, Statistical and Asymptotical Properties of Multivariate Data," IEEE Transactions on Geoscience and Remote Sensing, Vol. 37, No. 6, November 1999; Project in Pursuit in Hyperspectral Data Analysis, Jimenez & Landgrebe, November 23, 1999, pp. 1-32.--

Column 24,
Line 8, after "derived" and before "the" insert -- from --
Line 36, replace "an" with -- a --

Column 25,
Line 35, after "portion" and before "the" insert -- of --

Signed and Sealed this

Fifth Day of July, 2005

JON W. DUDAS
*Director of the United States Patent and Trademark Office*